United States Patent
Novotny et al.

(10) Patent No.: US 9,757,555 B2
(45) Date of Patent: Sep. 12, 2017

(54) PRE-MOLDED SUB-ASSEMBLIES FOR IMPLANTABLE MEDICAL LEADS

(71) Applicant: Medtronic, Inc., Minneapolis, MN (US)

(72) Inventors: Jeffrey M. Novotny, Bethel, MN (US); Jayesh R. Patel, Maple Grove, MN (US); Geetha Sethumadhavan, Plymouth, MN (US); Ivan J. Talledo, Blaine, MN (US); Ryan T. Bauer, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/692,470

(22) Filed: Apr. 21, 2015

(65) Prior Publication Data
US 2015/0306376 A1 Oct. 29, 2015

Related U.S. Application Data

(60) Provisional application No. 61/983,844, filed on Apr. 24, 2014.

(51) Int. Cl.
*A61N 1/00* (2006.01)
*A61N 1/05* (2006.01)
(Continued)

(52) U.S. Cl.
CPC .......... *A61N 1/05* (2013.01); *B29C 45/14622* (2013.01); *A61N 1/3752* (2013.01); (Continued)

(58) Field of Classification Search
CPC .. A61N 1/05; A61N 1/3752; B29C 45/14622; B29K 2101/12; B29L 2031/753; H01R 13/41; H01R 2201/12; H01R 24/58
See application file for complete search history.

(56) References Cited

U.S. PATENT DOCUMENTS

| | | | |
|---|---|---|---|
| 7,512,447 | B2 | 3/2009 | Marshall et al. |
| 8,250,754 | B2 | 8/2012 | Seifert |

(Continued)

FOREIGN PATENT DOCUMENTS

| | | |
|---|---|---|
| WO | 2008094879 A1 | 8/2008 |
| WO | 2011123608 A1 | 10/2011 |

OTHER PUBLICATIONS

International Search Report and Written Opinion of International Application No. PCT/US2015/027352, mailed Aug. 2015, 10 pp.
(Continued)

*Primary Examiner* — Lindsey G Wehrheim
(74) *Attorney, Agent, or Firm* — Shumaker & Sieffert, P.A.

(57) ABSTRACT

Pre-molded cylindrical sub-assemblies for inclusion in an implantable medical lead are described. The pre-molded cylindrical sub-assemblies comprise a cylindrical conductive element formed from a conductive material to define a substantially continuous interior surface and a substantially continuous exterior surface, and an insulative element formed from an insulative material molded onto the interior surface of the cylindrical conductive element. An interior surface of the insulative element defines a lumen of the pre-molded cylindrical sub-assembly configured to receive one or more elongated conductors of the implantable medical lead, and the cylindrical conductive element is configured to be electrically connected to one of the elongated conductors with the elongated conductors within the lumen. The cylindrical conductive element may act as an electrode, e.g., on a distal portion of the lead, or a connector, e.g., on a proximal portion of the lead.

30 Claims, 16 Drawing Sheets

(51) Int. Cl.
    *B29C 45/14*    (2006.01)
    *B29K 101/12*   (2006.01)
    *B29L 31/00*    (2006.01)
    *A61N 1/375*    (2006.01)
    *H01R 24/58*    (2011.01)
    *H01R 13/41*    (2006.01)

(52) U.S. Cl.
    CPC ..... *B29K 2101/12* (2013.01); *B29L 2031/753* (2013.01); *H01R 13/41* (2013.01); *H01R 24/58* (2013.01); *H01R 2201/12* (2013.01)

(56) References Cited

U.S. PATENT DOCUMENTS

| | | |
|---|---|---|
| 2003/0236562 A1 | 12/2003 | Kuzma |
| 2009/0254162 A1 | 10/2009 | Quinci et al. |
| 2013/0167372 A1 | 7/2013 | Black et al. |

OTHER PUBLICATIONS

International Preliminary Report on Patentability from International Application No. PCT/US2015/027352, mailed Nov. 3, 2016, 8 pp.

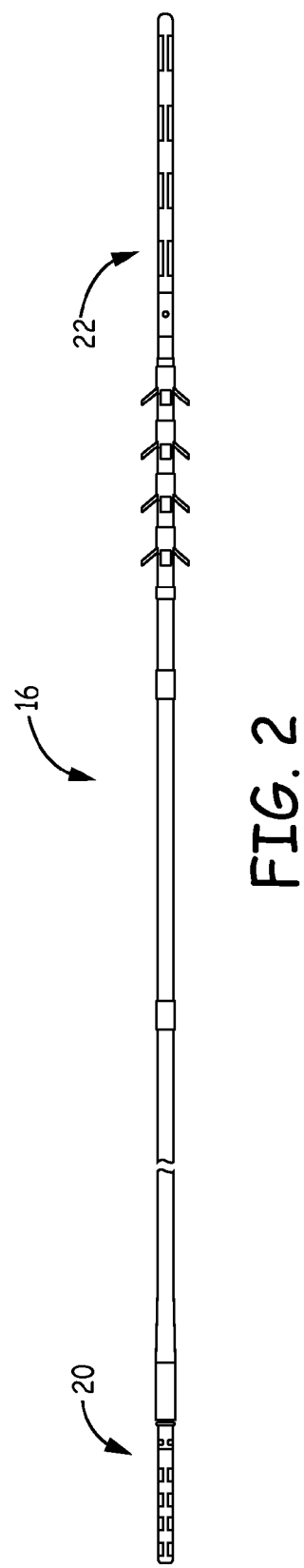

PRE-MOLDED SUB-ASSEMBLIES FOR IMPLANTABLE MEDICAL LEADS

This application claims the benefit of U.S. Provisional Application Ser. No. 61/983,844, entitled "PRE-MOLDED SUB-ASSEMBLIES FOR IMPLANTABLE MEDICAL LEADS," filed on Apr. 24, 2014, the entire content of which is incorporated herein by reference.

TECHNICAL FIELD

The disclosure relates to implantable medical devices, and in particular, to implantable medical leads configured to conduct electrical signals.

BACKGROUND

Implantable electrical stimulators may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. In general, an implantable stimulator delivers neurostimulation therapy in the form of electrical pulses. An implantable stimulator may deliver neurostimulation therapy via one or more leads that include electrodes located proximate to target tissues of the brain, the spinal cord, pelvic nerves, peripheral nerves, or the stomach of a patient. Hence, stimulation may be used in different therapeutic applications, such as deep brain stimulation (DBS), spinal cord stimulation (SCS), pelvic stimulation, gastric stimulation, or peripheral nerve stimulation. Stimulation also may be used for muscle stimulation, e.g., functional electrical stimulation (FES) to promote muscle movement or prevent atrophy.

Implantable medical leads carry electrodes that may be used to deliver electrical stimulation and/or sense electrical physiological signals. Different examples of implantable medical leads include cylindrical leads carrying ring electrodes or segmented electrodes and paddle style leads that carry electrode contacts. Paddle style leads may provide directional stimulation, but often require surgical implantation, although percutaneous implantation is possible. Cylindrical leads with ring or segmented electrodes may be implanted surgically or percutaneously.

In general, implantable medical leads include one or more electrodes at or near a distal end of the lead, e.g., on a distal portion of the lead, which may be positioned proximate the patient tissue to be stimulated and/or from which the physiological signals are to be sensed. Implantable medical leads also include one or more connectors at or near a proximal end of the lead, e.g., on a proximal portion of the lead. The connectors are electrically connected to a respective one or more of the electrodes by one or more conductors within the body of the lead. The connectors may be electrically connected to circuitry within an implantable medical device, e.g., via a header of the implantable medical device and, in some cases, via a lead extension. In some cases, the proximal portion of the lead, including the connectors, may be inserted into a receptacle of the header or lead extension to mechanically and electrically connect the lead to the implantable medical device.

SUMMARY

This disclosure includes techniques for the design, manufacture, and use of implantable medical leads including one or more pre-molded cylindrical sub-assemblies. Implantable medical leads including one or more pre-molded cylindrical sub-assemblies as described herein may be percutaneously implantable, and provide stimulation and/or sensing functionality via one or more electrodes, e.g., on a distal portion of the lead. The implantable medical leads may include one or more connectors, e.g., on a proximal portion of the lead, that electrically connect the one or more electrodes to an implantable medical device via one or more conductors within the leads.

The pre-molded cylindrical sub-assemblies may comprise a cylindrical conductive element formed from a conductive material, and an insulative element formed from an insulative material molded onto an interior surface of the cylindrical conductive element. An interior surface of the insulative element defines a lumen of the pre-molded cylindrical sub-assembly. The lumen of the pre-molded cylindrical sub-assembly may be configured to receive one or more elongated conductors of the implantable medical lead, e.g., longitudinally during assembly of the lead. The cylindrical conductive element is configured to be electrically connected one of the elongated conductors, e.g., while the conductors are within the lumen of the pre-molded cylindrical sub-assembly during assembly of the lead.

In some examples, a cylindrical conductive element may act as an electrode for the lead, e.g., on a distal portion of the lead configured to be implanted proximate target tissue of the patient for delivery of electrical stimulation or sensing of a physiological signal. In some examples, a cylindrical conductive element may act as a connector for the lead, e.g., on a proximal portion of the lead configured to be connected to an implantable medical device or a lead extension, and thereby configured to electrically connect the implantable medical device to an elongated conductor within the lead. In some examples, an implantable medical lead includes one or more pre-molded cylindrical sub-assemblies, and the cylindrical conductive elements of each of the pre-molded cylindrical sub-assemblies acts as an electrode or a connector for the lead. In some examples, each connector and electrode on an implantable lead is a cylindrical conductive element of one of a plurality of pre-molded cylindrical sub-assemblies of the implantable medical lead.

The insulative element of a pre-molded cylindrical sub-assembly may be configured to center the one or more elongated conductors within the lumen of the pre-molded cylindrical sub-assembly during assembly of the lead, e.g., during forming an overmold adjacent the one or more pre-molded cylindrical sub-assemblies and over the one or more elongated conductors. In some examples, the one or more elongated conductors are within insulation, e.g., an insulated helical conductor, and the insulative element of the pre-molded cylindrical sub-assembly is configured to prevent contact between the interior surface of the cylindrical conductive element and the insulation of the one or more elongated conductors. In this manner, the insulative element may protect against damage to the insulation of the elongated conductors, or to the conductors themselves, during overmolding, or otherwise during assembly of the lead. Damage to the insulation or conductor may result in an undesirable impedance condition, e.g., low impedance, for the electrode associated with the damaged insulation or conductor.

Additionally, the insulative element of a pre-molded cylindrical sub-assembly may be configured to bond to the overmold during forming of the overmold, e.g., by injection molding, adjacent the one or more pre-molded cylindrical sub-assemblies and over the one or more elongated conductors. For example, the material of the insulative element may at least partially reflow during molding of the overmold, and thereby intermix with the overmold material. Such bonding of the insulative element to the overmold may increase the tensile strength of the lead.

In one example, an implantable medical lead configured to conduct an electrical signal between an implantable medical device and tissue of a patient comprises one or more elongated conductors, and a proximal end comprising one or more connectors. Each of the connectors is electrically connected to at least one of the conductors, and each of the connectors is configured to electrically connect the at least one of the conductors to the implantable medical device. The implantable medical lead further comprises a distal end comprising one or more electrodes. Each of the electrodes is electrically connected to at least one of the conductors, and each of the electrodes is configured to electrically connect the at least one of the conductors to the tissue. The implantable medical lead further comprises one or more pre-molded cylindrical sub-assemblies. Each of the sub-assemblies comprises a cylindrical conductive element formed from a conductive material to define a substantially continuous interior surface and a substantially continuous exterior surface, wherein the cylindrical conductive element is one of the connectors or the electrodes or the implantable medical lead. Each of the sub-assemblies further comprises an insulative element formed from an insulative material molded onto the interior surface of the cylindrical conductive element, wherein an interior surface of the insulative element defines a lumen of the pre-molded cylindrical sub-assembly configured to receive the elongated conductors of the implantable medical lead, and the cylindrical conductive element is configured to be electrically connected to one of the elongated conductors with the elongated conductors within the lumen.

In another example, a pre-molded cylindrical sub-assembly for inclusion in an implantable medical lead configured to conduct an electrical signal between an implantable medical device and tissue of a patient comprises a cylindrical conductive element formed from a conductive material to define a substantially continuous interior surface and a substantially continuous exterior surface. The pre-molded cylindrical sub-assembly further comprises an insulative element formed from an insulative material molded onto the interior surface of the cylindrical conductive element, wherein an interior surface of the insulative element defines a lumen of the pre-molded cylindrical sub-assembly configured to receive one or more elongated conductors of the implantable medical lead, and the cylindrical conductive element is configured to be electrically connected to one of the elongated conductors with the elongated conductors within the lumen.

In another example, a method of manufacturing an implantable medical lead configured to conduct an electrical signal between an implantable medical device and tissue of a patient comprises manufacturing one or more pre-molded cylindrical sub-assemblies. Manufacturing each of the pre-molded cylindrical sub-assemblies comprises forming a cylindrical conductive element with a conductive material to define a substantially continuous interior surface and a substantially continuous exterior surface, and insert-molding an insulative material onto the interior surface of the cylindrical conductive element to form an insulative element, wherein an interior of the insulative element a lumen of the pre-molded cylindrical sub-assembly. Manufacturing each of the pre-molded cylindrical sub-assemblies further comprises longitudinally inserting one or more elongated conductors through the one or more lumens of the one or more pre-molded cylindrical sub-assemblies, and electrically connecting at least one of the elongated conductors to each of the cylindrical conductive elements of each of the pre-molded cylindrical sub-assemblies with the elongated conductor within the lumen. Each of the cylindrical conductive elements is one of a connector configured to electrically connect the conductor to an implantable medical device, or an electrode configured to electrically connect the conductors to the tissue.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIG. 2 is a conceptual diagram illustrating an example of an implantable medical lead.

DETAILED DESCRIPTION

Figure 1A:
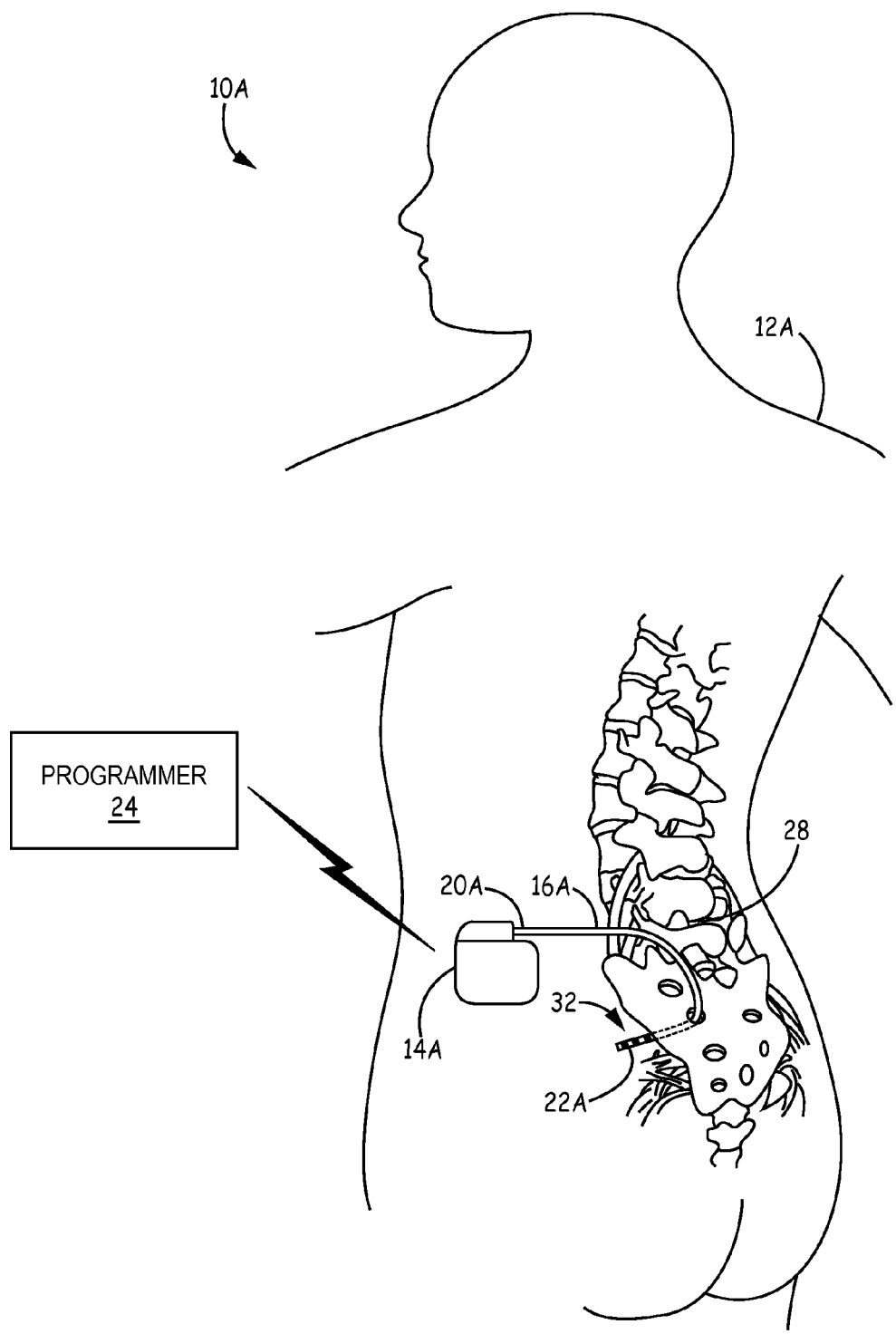
FIGS. 1A and 1B are conceptual diagrams illustrating example medical device systems that include implantable medical devices coupled to implantable medical leads.

The features and techniques described herein are useful in types of medical device systems, which include implantable medical leads and implantable medical devices. For example, the features and techniques described herein may be used in systems with implantable electrical stimulation leads and implantable medical devices that deliver electrical stimulation therapy to a patient's brain (e.g., DBS). In another example, the features and techniques described herein may be used in systems with medical devices that deliver electrical stimulation therapy to a patient's heart (e.g., pacemakers, and pacemaker-cardioverter-defibrillators). As other examples, the features and techniques described herein may be embodied in systems that deliver other types of electrical stimulation therapy (e.g., spinal cord stimulation, peripheral nerve stimulation, pelvic nerve stimulation, gastric nerve stimulation or vagal nerve stimulation), stimulation of at least one muscle or muscle groups, stimulation of at least one organ such as gastric system stimulation, stimulation concomitant to gene therapy, and, in general, stimulation of any tissue of a patient.

In addition, while the examples shown in the figures include leads coupled at their proximal ends to a stimulation therapy controller (e.g., implantable medical device or IMD) located remotely from the electrodes, other configurations are also possible and contemplated. In some examples, a lead comprises a portion of a housing, or a member coupled to a housing, of stimulation generator located proximate to or at the stimulation site (e.g., as a microstimulator). In other examples, a lead comprises a member at stimulation site that is coupled by a lead extension to an IMD.

During manufacturing, damage to the elongated conductors can occur during assembly of the conductive elements (i.e., connectors and/or electrodes) onto the elongated conductors, which can lead to a low impedance condition. One advantage that may result from use of a pre-molded cylindrical sub-assembly according to the techniques of this disclosure is the protection of the elongated conductors during lead assembly and the maximization of the distance from the elongated conductors to the conductive element due to better centering of the elongated conductors within the pre-molded cylindrical sub-assemblies. Another advantage that may result from use of a pre-molded cylindrical sub-assembly according to the techniques of this disclosure is improved AC impedance performance, e.g., due to avoiding damage to the elongated conductors or their insulation during lead assembly.

Another advantage that may result from use of a pre-molded cylindrical sub-assembly according to the techniques of this disclosure is that adhesive or separate reflowing of the insulative material on the interior of the pre-molded cylindrical sub-assembly may not be necessary to achieve desired mechanical properties of the lead, such as tensile strength. Another advantage that may result from use of a pre-molded cylindrical sub-assembly according to the techniques of this disclosure is that the insulation layer may be increased, e.g., due to the presence the insulative layer of the pre-molded cylindrical sub-assembly, and bonding of the insulative layer to the insulation of the elongated conductors, which may provide increased tensile strength and improved performance under high electrical potential conditions, e.g., an improved hipot yield. Another advantage that may result from use of a pre-molded cylindrical sub-assembly according to the techniques of this disclosure is the potential for improved straightness due to centering of the conductors, e.g., coiled conductors, at the proximal and distal ends of the implantable medical lead.

Figure 1B:
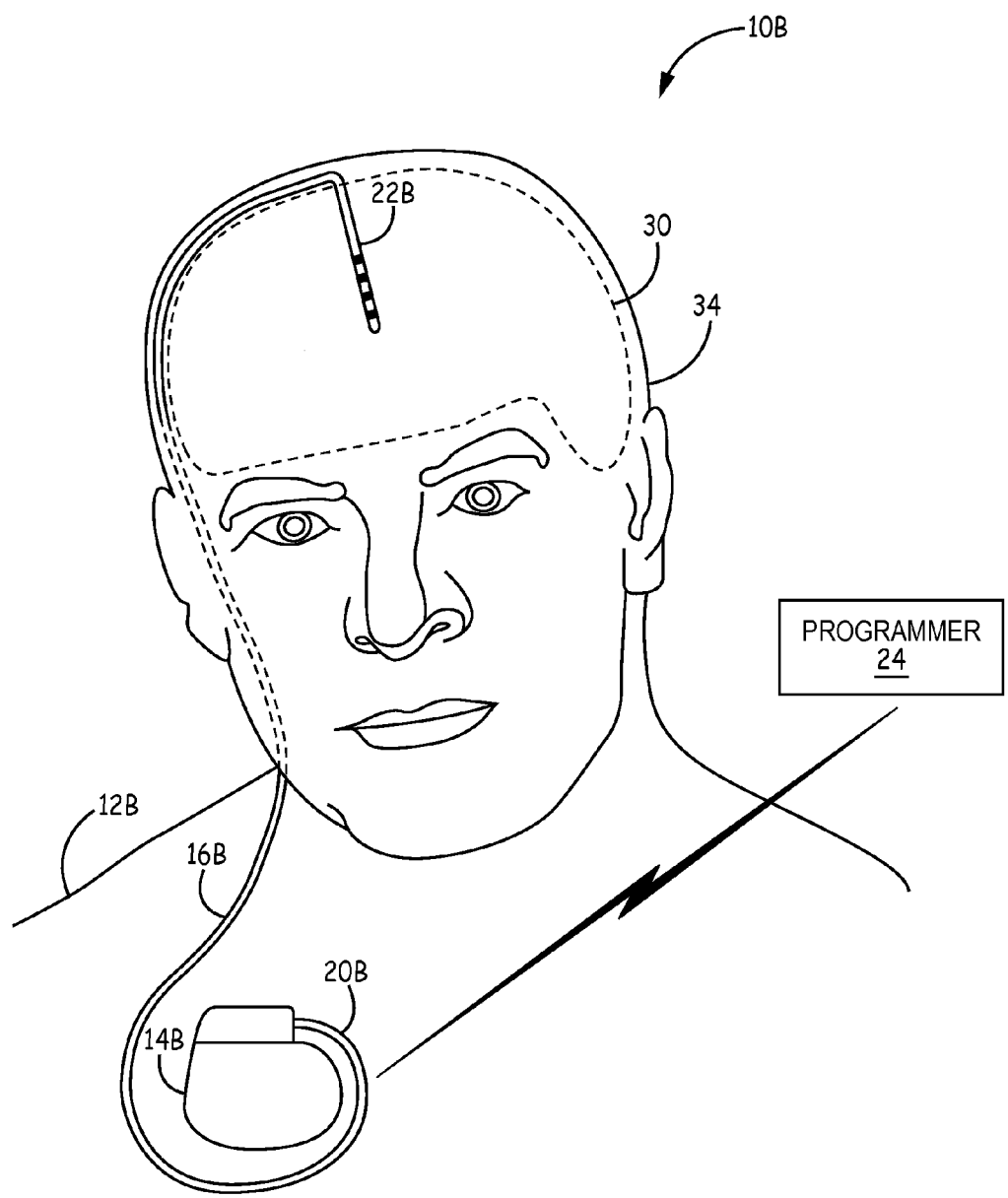

FIGS. 1A and 1B are conceptual diagrams illustrating example medical device systems 10A and 10B (collectively, "medical device systems 10") that include implantable medical devices coupled to implantable medical leads. In the example of FIG. 1A, system 10A includes an implantable medical device (IMD) 14A configured to deliver therapy to and/or sense physiological signals from target tissue including or near spinal cord 28 and/or pelvic nerves 32 of patient 12A through lead 16A. More particularly, IMD 14A may deliver electrical stimulation and sense electrical signals via electrodes at distal end 22A of lead 16A. The stimulation and signals may be conducted between the electrodes and IMD 14A by conductors within lead 16A, which are electrical connected to IMD 14A by connectors at proximal end 20A of lead 16A.

In the example of FIG. 1B, system 10B includes an IMD 14B configured to deliver therapy to and/or sensing physiological signals from brain 30 of patient 12B through lead 16B. More particularly, IMD 14B may deliver electrical stimulation and sense electrical signals via electrodes at distal end 22B of lead 16B. The stimulation and signals may be conducted between the electrodes and IMD 14B by conductors within lead 16B, which are electrical connected to IMD 14B by connectors at proximal end 20B of lead 16B.

IMDs 14A and 14B (collectively "IMDs 14") may include electronics and other internal components necessary or desirable for providing the functionality described herein as being associated with the device. In one example, IMDs 14 include one or more processors, memory, a signal generator, a sensing module, a telemetry module, and a power source. In general, memory of an IMD 14 may include computer-readable instructions that, when executed by a processor of the IMD, cause it to perform various functions attributed to the device herein. For example, a processor of an IMD 14 may control the signal generator and sensing module according to instructions and/or data stored on memory to deliver therapy to patient 12, sense physiological signals of the patient, and perform other functions related to treating condition(s) of the patient with IMD 14.

The signal generator of IMD 14 may generate electrical stimulation that is delivered to patient 12 via electrode(s) on one or more of leads 16, in order to provide, e.g., DBS, spinal cord stimulation, or other neurostimulation. The sensing module of IMD 14 may monitor electrical signals from electrode(s) on leads 16 of IMD 14 in order to monitor electrical activity of the patient, e.g., to monitor electrical signals generated by brain 30, other neurological signals or action potentials, or cardiac signals. A telemetry module of IMD 14 may include any suitable hardware, firmware, software or any combination thereof for communicating with another device, such as programmer 24. Under the control of a processor of IMD 14, the telemetry module may receive downlink telemetry from and send uplink telemetry to programmer 24 with the aid of an antenna, which may be internal and/or external.

Programmer 24 may be a handheld computing device, computer workstation, or networked computing device. Programmer 24 may include electronics and other internal components necessary or desirable for executing the functions associated with the device. In one example, programmer 24 includes one or more processors and memory, as well as a user interface, telemetry module, and power source.

As shown in FIG. 1A, medical device system 10A includes an IMD 14A, which is coupled to lead 16A having a proximal end 20A and a distal end 22A, and programmer 24. Lead 16A, for example, may be implanted near the spinal cord 28, pelvic nerves 32 (e.g., a pudendal nerve or sacral nerve), or any other nervous or muscle tissue that may be stimulated or from which physiological signals may be sensed. IMD 14A may be, for example, an implantable neurostimulator that provides electrical signals to patient 12A via electrodes located on a distal portion of lead 16A. IMD 14A may provide neurostimulation to treat symptoms of patient 12A, such as pain, fecal or urinary incontinence, erectile dysfunction, or other sexual dysfunction.

As shown in FIG. 1B, medical device system 10B includes IMD 14B and lead 16B implanted within patient 12B. Lead 16B includes proximal end 20B and distal end 22B. Specifically, lead 16 enters through cranium 34 and is implanted within brain 30 of patient 12B to deliver deep brain stimulation (DBS). One or more electrodes at distal end 22B of lead 16B provide electrical pulses to surrounding anatomical regions of brain 30 in a therapy that may alleviate a condition of patient 12. In some examples, more than one lead 16 may be implanted within brain 30 of patient 12 to stimulate multiple anatomical regions of the brain.

DBS may be used to treat dysfunctional neuronal activity in the brain which manifests as diseases or disorders such as Huntington's Disease, Parkinson's Disease, or movement disorders. The exact reasons why electrical stimulation therapy is capable of treating such conditions of the brain is unknown, but symptoms of these diseases can be lessened or eliminated with electrical stimulation therapy. Certain anatomical regions of brain 30 are responsible for producing the symptoms of such brain disorders. As one example, stimulating an anatomical region, such as the Substantia Nigra, in brain 30 may reduce the number and magnitude of tremors experienced by patient 12. Other anatomical regions may include the subthalamic nucleus, globus pallidus interna, ventral intermediate, and zona inserta. Anatomical regions such as these are targeted by the clinician during the implantation of lead 16. In other words, the clinician may attempt to position the distal portion of lead 16B, including the one or more electrodes, as close to these regions as possible.

FIG. 2 is a conceptual diagram illustrating an example of an implantable medical lead 16, which may correspond to either lead 16A of FIG. 1A or lead 16B of FIG. 1B. In the example of FIG. 2, lead 16 is illustrated as including proximal end 20 with connectors configured to electrically connect elongated conductors within the lead to an IMD, and distal end 22 with electrodes configured to electrically connect the conductors to patient tissue, as described in greater detail in FIGS. 3A-4B. In the example of FIG. 2, lead 16 is also illustrated as including fixation structures, which may be used, e.g., in lead 16A of FIG. 1A, to fix distal end 22 proximate to target tissue for delivery of stimulation or sensing via the electrodes. However, leads 16 according to this disclosure are not limited to the illustrated fixation structures, or to leads that include fixation structures. For example, lead 16B used as a DBS lead as illustrated in FIG. 1B may, in some examples, not include fixation structures.

In some examples, proximal end 20 and distal end 22 may have an overmold adjacent to and surrounding the connectors and/or electrodes. The overmold may, however, leave the connectors and electrodes exposed. The overmold may be a hardenable organic polymeric material selected from a group consisting of polyurethanes, polyurethanes with surface-modifying end groups, polyurethane silicone block copolymers, silicones, fluoropolymers, fluoroelastomers, polyethylenes, and polyesters, as examples.

Figure 3A:
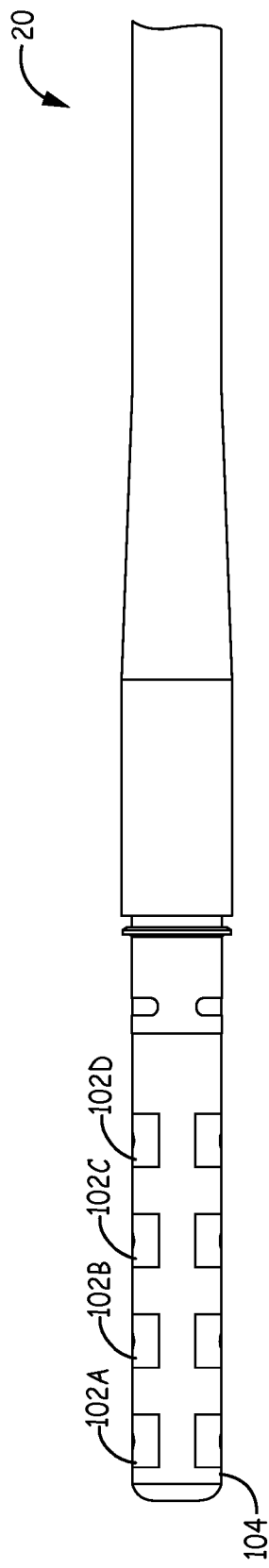
FIGS. 3A and 3B are perspective and cross-sectional diagrams, respectively, illustrating an example configuration of a proximal end of an implantable medical lead.
Figure 3B:
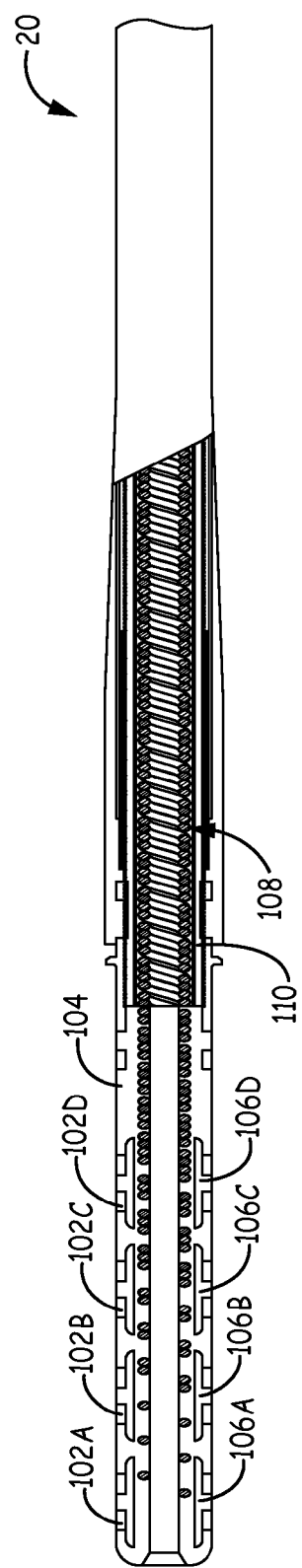

FIGS. 3A and 3B are perspective and cross-sectional diagrams, respectively, illustrating an example configuration of proximal end 20 of an implantable medical lead 16. In the example of FIGS. 3A-3B, proximal end 20 includes one or more connectors 102A-102D, an overmold 104, insulative elements 106A-106D, one or more elongated conductors 108, and an insulator 110 of the one or more elongated conductors.

Figure 6A:
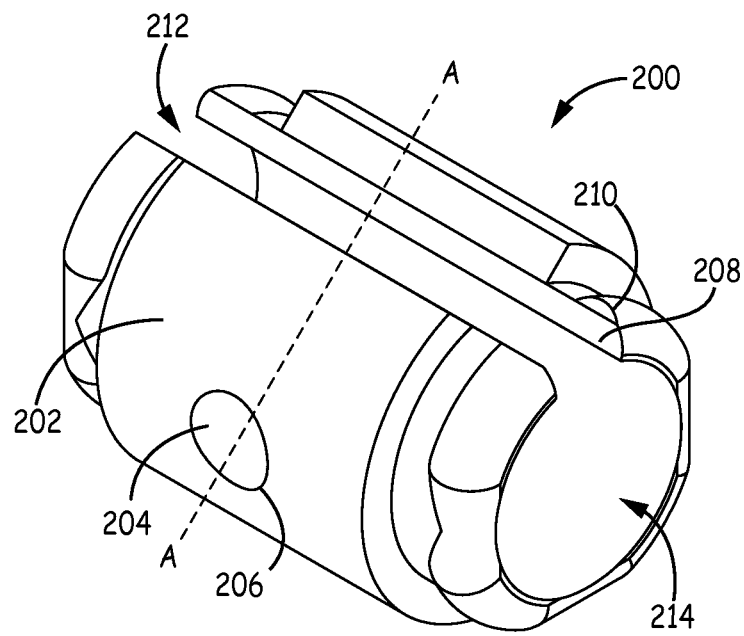
FIGS. 6A-6D are perspective and cross-sectional diagrams illustrating an example a pre-molded cylindrical connector sub-assembly.

Each of connectors 102A-102D (collectively, "connectors 102") is a cylindrical conductive element that is part of a pre-molded cylindrical sub-assembly (e.g., pre-molded cylindrical sub-assembly 200 as described in FIG. 6A). The pre-molded cylindrical sub-assemblies also include the corresponding insulative elements 106A-106D (collectively, "insulative elements 106"). In the example of FIGS. 3A-3B, connectors 102 provide an electrical connection between IMD 14 and elongated conductors 108 of lead 16. In some examples, connectors 102 may be formed from a conductive biocompatible material such as a platinum alloy, stainless steel, or other metal.

Overmold 104 is adjacent to and surrounds connectors 102, and provides support and electrical isolation between each of connectors 102. In some examples, overmold 104 is a hardenable organic polymeric material, which is injected into a mold containing lead 16, and fills in the interstices of proximal end 20. In some examples, after hardening the organic polymeric material to create overmold 104 at proximal end 20, a portion of overmold 104 may be trimmed and/or removed to expose connector 102, such that connector 102 may have an electrical connection with IMD 14. In some examples, the hardenable organic polymeric material may be selected from a group consisting of polyurethanes, polyurethanes with surface-modifying end groups, polyurethane silicone block copolymers, silicones, fluoropolymers, fluoroelastomers, polyethylenes, and polyesters. In other words, overmold 104 exposes the cylindrical conductive elements of connectors 102 while providing support and isolation between connectors 102, and protecting the interior of proximal end 20 from external conditions. In some examples, overmold 104 may also aid in retaining connectors 102 in their respective positions.

Insulative elements 106A-106D (collectively "insulative elements 106") are part of a pre-molded cylindrical sub-assembly (e.g., cylindrical sub-assembly 200 as described in FIG. 6A), and provide support and isolation between connectors 102 and elongated conductors 108. In some examples, insulative elements 106 are formed from a hardenable organic polymeric material, which is injected into a mold along with connectors 102. The hardenable organic polymeric material of insulative elements 106 may be selected from a group consisting of polyurethanes, polyurethanes with surface-modifying end groups, polyurethane silicone block copolymers, silicones, fluoropolymers, fluoroelastomers, polyethylenes, and polyesters. In various examples, the materials, e.g., hardenable organic polymers, of insulative elements 106 and overmold 104 can be different or the same. Better bonding may occur in some instances where the overmold material of overmold 104 has a higher melting point than the insulative material of insulative elements 106.

In some examples, after hardening the organic polymeric material to create the pre-molded cylindrical sub-assembly, a portion of insulative element 106 may be trimmed and/or removed to define a lumen of the pre-molded cylindrical sub-assembly, such that the sub-assembly may receive elongated conductors 108, which provide an electrical connection between electrodes (e.g., electrodes 122A-122D of FIGS. 4A and 4B) and connectors 102. In some examples, a mandrel is included in the mold within a lumen defined by connector 102, and the insulative material of insulative element 106 may be introduced into the mold between an interior surface of connector 102 and the mandrel. In this manner, the mandrel may define the interior surface of insulative element 106, and accordingly the lumen of the pre-molded cylindrical sub-assembly including connector 102 and insulative element 106. In these and other examples, insulative element 106 of a pre-molded cylindrical sub-assembly may define a lumen of the pre-molded cylindrical sub-assembly for receiving elongated conductors 108, and support connector 102 or another cylindrical conductive element, while also isolating connector 102 from elongated conductors 108. In some examples, insulative element 106 may also aid in centering elongated conductors 108 relative to connector 102 as connector 102 is positioned along the longitudinal axis of elongated connectors 108

Figure 4A:
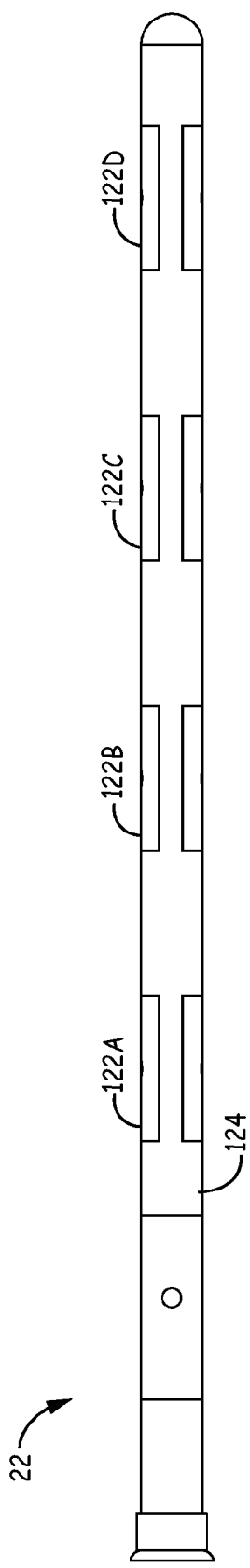
FIGS. 4A and 4B are perspective and cross-sectional diagrams, respectively, illustrating an example configuration of a distal end of an implantable medical lead.
Figure 4B:
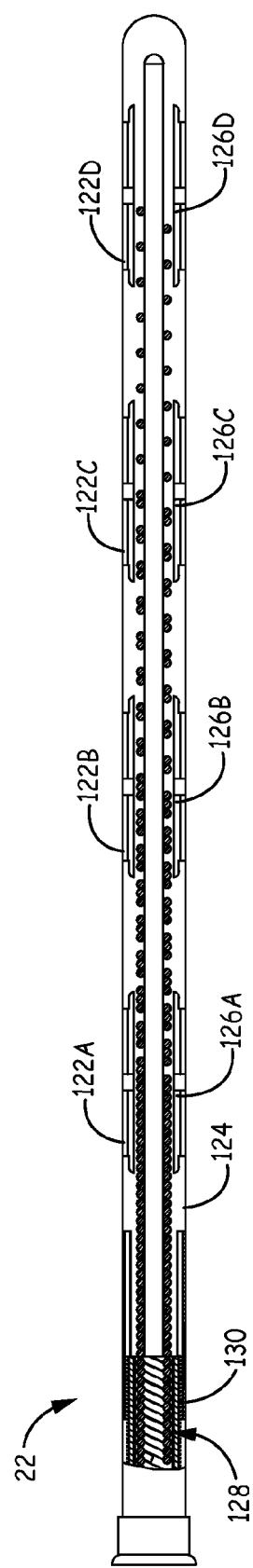

Elongated conductors 108 in FIG. 3B are a representation of insulated electrical conductors electrically connecting one or more connectors 102 to one or more electrodes (e.g., electrodes 122A-122D of FIGS. 4A and 4B). In the example of FIG. 3B, elongated conductors 108 are within insulator 110, which provides support and isolation to one or more elongated conductors 108. In some examples, elongated conductors 108 may be coiled within insulator 110, e.g., co-radially, to form insulated helical conductors. Insulator 110 of conductors 108, although present, is not shown at the distal portion of conductors 108 in FIG. 3B to illustrate the termination of respective ones of the conductors at respective ones of connectors 102, i.e., until one of conductors 108 is present at connector 102A. The configuration, type, and number of elongated conductors 108 is not limited to the example illustrated in FIG. 3B and, in other examples, lead 16 as described in FIGS. 1A-2 may include any configuration, type, and number of conductors. In some examples, one elongated conductor 108 may electrically couple at least two electrodes to one or more connectors 102. In the example of FIG. 3B, each connector 102 is electrically connected to one of elongated conductors 108. Each of elongated conductors 108 may extend between one or more electrodes at a distal end 22 of a lead 16 and one of connectors 102 at proximal end 20 of a lead. In some examples, proximal end 20 of lead 16 may have a substantially circular cross-sectional shape, although other cross-sectional shapes may also be used.

In some examples, connectors 102 of lead 16 may be electrically connected to an IMD 14 with a stimulation generator configured to deliver electrical stimulation via a selected combination of one or more electrodes of lead 16. In such examples, connectors 102 of lead 16 may be electrically connected to the stimulation generator. In some examples, connectors 102 of lead 16 may be electrically connected to an IMD 14 with a sensing module configured to sense electrical signals of a patient via a selected combination of one or more electrodes of lead 16. In such examples, connectors 102 of lead 16 may be electrically connected to the sensing module. In some examples, the IMD includes both a signal generator and a sensing module, and each connector 102 of lead may be electrically connected to the signal generator and sensing module.

FIGS. 4A and 4B are perspective and cross-sectional diagrams, respectively, illustrating an example configuration of distal end 22 of an implantable medical lead. In the examples of FIGS. 4A-4B, distal end 22 includes one or more electrodes 122A-122D, an overmold 124, insulative elements 126A-126D, one or more elongated conductors 128, and an insulator 130 of the one or more elongated conductors.

Figure 7A:
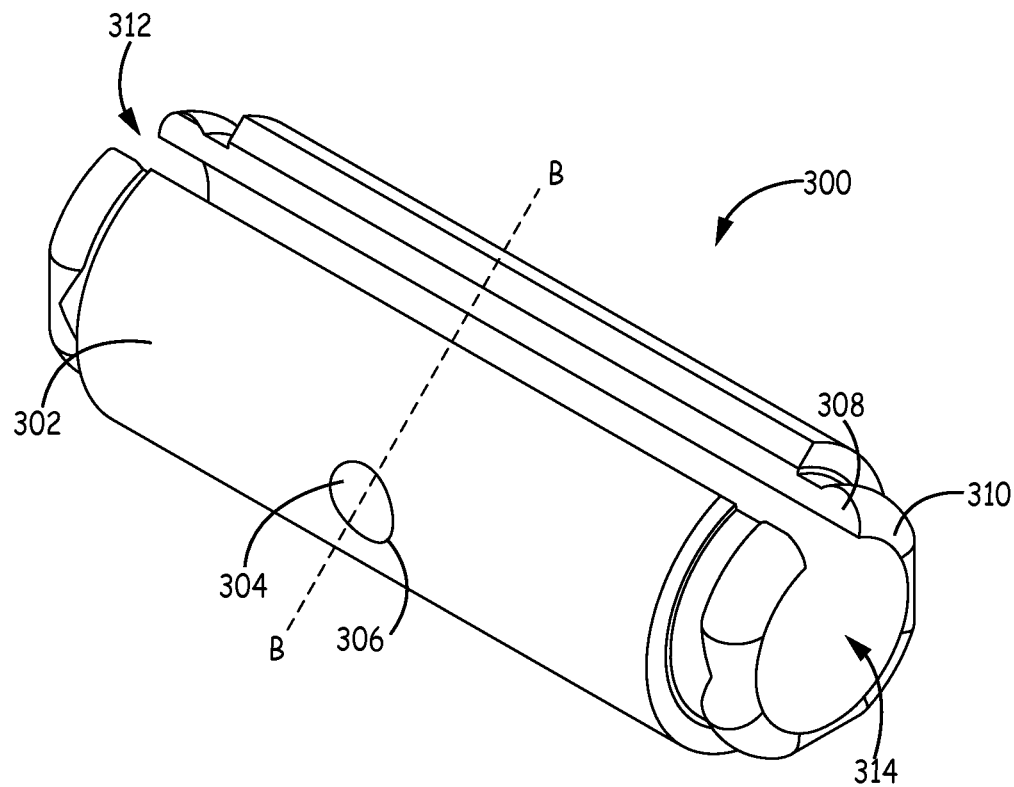
FIGS. 7A-7D are perspective and cross-sectional diagrams illustrating an example of a pre-molded cylindrical electrode sub-assembly.

Each of electrodes 122A-122D (collectively "electrodes 122") is a cylindrical conductive element that is part of a pre-molded cylindrical sub-assembly (e.g., pre-molded cylindrical sub-assembly 300 as described in FIG. 7A). The pre-molded cylindrical sub-assemblies also include the corresponding insulative elements 126A-126D (collectively "insulative elements 126"). In the example of FIGS. 4A-4B, electrodes 122 provide an electrical connection between tissue or organs of a patient and IMD 14 via one or more elongated conductors 128 of lead 16. In some examples, electrodes 122 may be formed from a conductive biocompatible material such as a platinum alloy, stainless steel, or other metal.

Overmold 124 is adjacent to and surrounds electrodes 122, and provides support and electrical isolation between each of electrodes 122. In some examples, overmold 124 is a hardenable organic polymeric material, which is injected into a mold containing lead 16, and fills in the interstices of distal end 22. In some examples, overmold 124 shown with respect to distal end 22 in FIGS. 4A and 4B is the same as overmold 104 shown with respect to proximal end 20 of lead 16 in FIGS. 3A and 3B, i.e., is a substantially continuous overmold applied to the entire lead during a molding process. In some examples, after hardening the organic polymeric material to create overmold 124 at distal end 22, a portion of overmold 124 may be trimmed and/or removed to expose electrodes 122, such that electrodes 122 may have an electrical connection patient tissue. In other examples, outer surfaces of electrodes 122 may be adjacent to the mold, such that the outer surfaces of electrodes 122 remain exposed and require no trimming or removal of overmold material. In some examples, the hardenable organic polymeric material ("overmold material") may be selected from a group consisting of polyurethanes, polyurethanes with surface-modifying end groups, polyurethane silicone block copolymers, silicones, fluoropolymers, fluoroelastomers, polyethylenes, and polyesters. In other words, overmold 124 exposes the cylindrical conductive elements of electrodes 122 while providing support and electrical isolation between electrodes 122, and protecting the interior of distal end 22 from external conditions. In some examples, overmold 124 may also aid in retaining electrodes 122 in their respective positions.

Insulative elements 126A-126D are part of a pre-molded cylindrical sub-assembly (e.g., pre-molded cylindrical sub-assembly 300 as described in FIG. 7A), and provide support and isolation between electrodes 122 and elongated conductors 128. In some examples, insulative elements 126 are formed from a hardenable organic polymeric material, which is injected into a mold along with electrodes 122. In various examples, the materials, e.g., hardenable organic polymers, of insulative elements 126 and overmold 124 can be different or the same. Better bonding may occur in some instances where the overmold material of overmold 124 has a higher melting point than the insulative material of insulative elements 126.

In some examples, after hardening the organic polymeric material to create the cylindrical sub-assembly, a portion of insulative element 126 may be trimmed and/or removed to define a lumen of the pre-molded cylindrical sub-assembly, such that the sub-assembly may receive elongated conductors 128, which provide an electrical connection between electrodes 122 and IMD 14 via connectors 102. In some examples, a mandrel is included in the mold within a lumen defined by an electrode 122, and the insulative material of the insulative element 126 may be introduced into the mold between an interior surface of the electrode 122 and the mandrel. In this manner, the mandrel may define the interior surface of the insulative element 126, and accordingly the lumen of the pre-molded cylindrical sub-assembly including the electrode and the insulative element 126. In these and other examples, insulative elements 126 define a lumen for receiving elongated conductors 128, and support the cylindrical conductive element, i.e., electrode 122, while also electrically isolating electrode 122 from one or more elongated conductors 128. In some examples, insulative element 126 may also aid in centering electrode 122 as electrode 122 is positioned at distal end 22 along the longitudinal axis of elongated connectors 128.

Elongated conductors 128 in FIG. 4B are a representation of insulated electrical conductors (e.g., wires) coupling one or more electrodes 122 to one or more connectors (e.g., connectors 102A-102D of FIGS. 3A and 3B). In the example of FIG. 4B, elongated conductors 128 are within insulator 130, which provides support and electrical isolation to one or more elongated conductors. In some examples, elongated conductors 128 may be coiled within insulator 130, e.g., co-radially, to form insulated helical conductors. Insulator 130 of conductors 128, although present, is not shown at the distal portion of conductors 128 in FIG. 4B to illustrate the termination of respective ones of the conductors at respective ones of electrodes 122, i.e., until a one of conductors 128 is present at electrode 122A. Elongated conductors 128 and insulator 130 illustrated with respect to distal end 22 in FIGS. 4A and 4B may be the same as elongated conductors 108 and insulator 110 illustrated with respect to proximal end 20 in FIGS. 3A and 3B, i.e., may be the same elongated conductors within insulation extending between and electrically connecting respective connectors 102 at a proximal end 20 of lead 16 to respective electrodes 122 at a distal end 22 of the lead 16.

The configuration, type, and number of elongated conductors 128 is not limited to the example illustrated in FIG. 4B and, in other examples, lead 16 as described in FIGS. 1A-2 may include any configuration, type, and number of conductors. In some examples, one elongated conductor 128 may electrically couple at least two connectors to one or more electrodes 122. In the example of FIG. 4B, each electrode 122 is electrically connected to one of elongated conductors 128. Each of elongated conductors 128 may extend between one or more electrodes 122 at a distal end 22 of a lead 16 and one of connectors 102 at proximal end 20 of a lead. In some examples, distal end 22 of lead 16 may have a substantially circular cross-sectional shape, although other cross-sectional shapes may also be used.

In some examples, electrodes 122 of lead 16 may be electrically connected to an IMD 14 with a stimulation generator configured to deliver electrical stimulation via a selected combination of one or more of the electrodes. In such examples, electrodes 122 of lead 16 may be electrically connected to the stimulation generator, e.g., via respective conductors 128 and connectors 102. In some examples, electrodes 122 of lead 16 may be electrically connected to an IMD 14 with a sensing module configured to sense electrical signals of a patient via a selected combination of one or more of the electrodes. In such examples, electrodes 122 of lead 16 may be electrically connected to the sensing module, e.g., via respective conductors 128 and connectors 102. In some examples, the IMD includes both a signal generator and a sensing module, and each electrode of lead 16 may be electrically connected to the signal generator and sensing module, e.g., via respective conductors 128 and connectors 102.

Figure 5A:
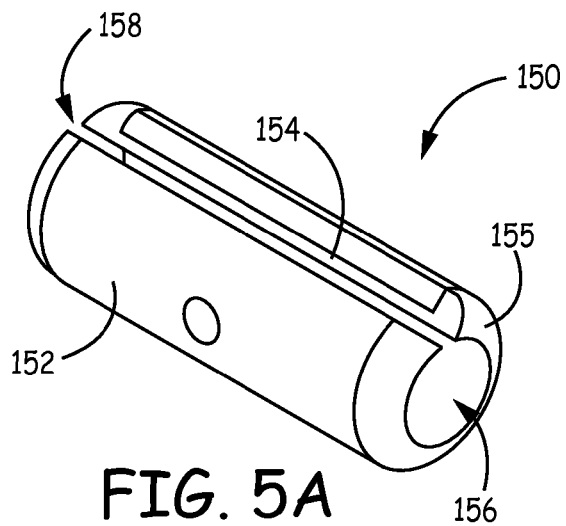
FIGS. 5A-5C are perspective diagrams illustrating an example of a pre-molded cylindrical sub-assembly of an implantable medical lead.
Figure 5B:
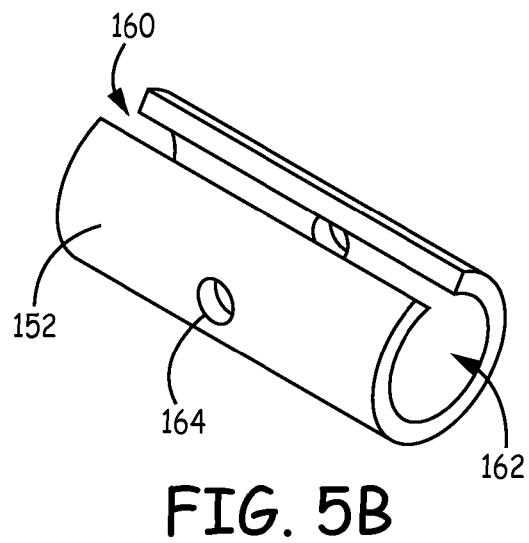
Figure 5C:
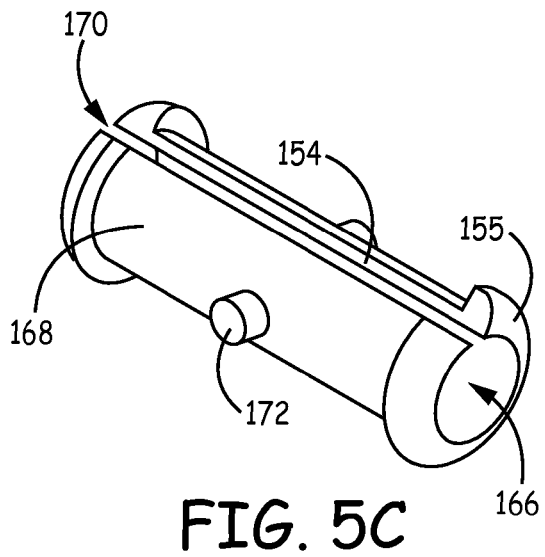

FIGS. 5A-5C are perspective diagrams illustrating an example pre-molded cylindrical sub-assembly 150 of an implantable medical lead. In the example of FIG. 5A, pre-molded cylindrical sub-assembly 150 includes a cylindrical conductive element 152 and an insulative element 154, which define a lumen 156 and a gap 158.

Pre-molded cylindrical sub-assembly 150 centers cylindrical conductive element 152, which may be connector 102 or electrode 122, without cylindrical conductive element 152 touching one or more insulated elongated conductors during assembly and before an uninsulated portion of the insulated elongated conductors is attached to cylindrical conductive element 152. Pre-molded cylindrical sub-assembly 150 may also provide an improvement of AC impedance because of the increased distance of cylindrical conductive element 152 from one or more insulated elongated conductors and the insulative properties of insulative element 154.

Cylindrical conductive element 152 is formed of a conductive biocompatible material, which can deliver electrical stimulation for therapy to and/or receive electrical signals from patient tissue proximate the cylindrical conductive element. As illustrated in FIG. 5B, cylindrical conductive element 152 is formed to define a substantially continuous interior surface and a substantially continuous exterior surface, such that the substantially continuous interior surface and exterior surface allows for an insulative material to be injected into the interior of the cylindrical conductive element 152 to create pre-molded cylindrical sub-assembly 150. The substantially continuous cylindrical inner and outer surfaces of cylindrical conductive element 152 are different than the non-continuous surfaces that may define a cylinder, such as a segmented electrode having plurality of discrete electrode segments arranged about a circumference of a lead, or a coil electrode (e.g., defibrillation electrode) formed from an elongated conductor coiled about the circumference of a lead. In some examples, cylindrical conductive element 152 may be a connector, which electrically connects IMD 14 to lead 16, or an electrode, which electrically connects tissue or organs to lead 16.

Insulative element 154 is formed by an insulative material on the interior surface of cylindrical conductive element 152, and can support and electrically isolate cylindrical conductive element 152 from an elongated conductor. Insulative element 154 may be formed by injecting an insulative material into cylindrical conductive element 152, e.g., onto the substantially continuous inner surface of the conductive element, and processing the insulative material to define lumen 156 along a longitudinal axis and gap 158. For example, the insulative material may be processed by a mandrel to create lumen 156. In another example, the insulative material may processed by trimming the insulative material, e.g., with a blade, mold tooling, or laser ablation, to create gap 158.

Insulative element 154, in some examples, may also extend beyond the outer surface at one or both ends of cylindrical conductive element 152 to form cap 155. Cap 155 may be used to isolate the ends of cylindrical conductive element 152, and cap 155 may further electrically isolate cylindrical conductive element 152 from an elongated conductor (not shown) and other cylindrical conductive elements. In some examples, cap 155 may be part of insulative element 154 that tapers away from an end of cylindrical conductive element 152. Insulative element 154 may also be of varying dimensions to improve the support and electrical isolation of cylindrical conductive element 152, and to minimize the potential of damaging one or more elongated conductors. In some examples, insulative element 154 keeps pre-molded cylindrical sub-assembly 150 centered during injection molding of the overmold (e.g., overmolds 104 and 124 as described in FIGS. 3A-4B). In some examples, such as illustrated in FIG. 5C, insulative element 154 is a substantially cylindrical insulative element 154 molded onto substantially all of the interior surface of the substantially cylindrical conductive element 152, and the substantially cylindrical insulative element defines a substantially continuous interior surface that defines lumen 156 of pre-molded cylindrical sub-assembly 150.

Lumen 156 is an aperture along a longitudinal axis of pre-molded cylindrical sub-assembly 150, and is configured to receive an elongated conductor (not shown). In some examples, lumen 156 may be used to center cylindrical conductive element 152 along lead 16. In some examples, lumen 156 of pre-molded cylindrical sub-assembly 150 corresponds to lumen 166 (FIG. 5C) of insulative element 154. Lumen 166 of insulative element 154 may be created by inserting a mandrel into a lumen 162 (FIG. 5B) of cylindrical conductive element 152 during forming of insulative element 154 onto the interior surface of cylindrical conductive element 152 and over the mandrel.

Gap 158 is a gap created by a combination of a first gap 160 (FIG. 5B) in cylindrical conductive element 152 and a second gap 170 (FIG. 3C) in insulative element 154. In some examples, gap 170 in insulative element 154 is created by trimming the insulative material e.g., with a blade, mold tooling, or laser ablation, after the insulative material has been hardened. In other examples, the second gap in cylindrical insulative element 154 is created by removing the insulative material before the insulative material has been hardened. In some examples, gap 158 may, as illustrated in FIG. 5A, be a longitudinal channel. Gap 158 may allow access to elongated conductors 108, 128 as described in FIGS. 3A-4B while the conductors are positioned within lumen 156 during assembly of lead 16, to allow electrical connection of one of the conductors to the cylindrical conductive element 152, e.g., via resistance welding. Gap 158 may facilitate such electrical connection without the need to unwind each conductor, e.g., each filer. In some examples, each of a plurality of pre-molded cylindrical sub-assemblies 150 may be positioned longitudinally along an elongated conductor, and gaps 158 may facilitate collective electrical connection of the cylindrical conductive elements 152 in this arrangement, rather than individual positioning and electrical connection as a two-step process repeated for each of the pre-molded cylindrical sub-assemblies 150.

As illustrated in FIG. 5B, cylindrical conductive element 152 defines a gap 160, lumen 162, and injection molding aperture 164. Gap 160 allows an elongated conductor (not shown) to be attached (e.g., welded) to provide an electrical connection between cylindrical conductive element 152 and IMD 14. In some examples, gap 160 may be within a range of widths from approximately 0.004 inches to approximately 0.025 inches. Lumen 162 is an aperture along the longitudinal axis of cylindrical conductive element 152 and is defined by a substantially continuous interior surface of cylindrical conductive element 152. In some examples, lumen 162 is configured to be an aperture with a diameter capable of receiving both cylindrical insulative element 154 and an elongated conductor (not shown). For example, the diameter of lumen 162 may within a range from approximately 0.020 inches to approximately 0.045 inches.

Injection molding aperture 164 is an aperture, which allows for an insulative material to be injected into cylindrical conductive element 152 and onto the interior surface of cylindrical conductive element 152 to form pre-molded cylindrical sub-assembly 150 as described in FIG. 5A. In the example of FIG. 5B, injection molding aperture 164 is positioned on two sides of cylindrical conductive element 152 midway along the longitudinal axis and perpendicular to a vertical plan through gap 160. However, injection molding aperture 164 may located anywhere that allows insulative material to be injected into cylindrical conductive element 152. In some examples, rather than a separate injection molding aperture 164, insulative material to form insulative element 154 may be introduced through lumen 162 or gap 160.

In the example of FIG. 5C, insulative element 154 includes lumen 166, outer insulative surface 168, gap 170, and protrusion 172. Lumen 166 is an aperture along the longitudinal axis of insulative element 154 and may be defined by a substantially continuous interior surface of insulative element 154. In some examples, lumen 166 is configured to be an aperture with a diameter capable of receiving one or more insulated elongated conductors (not shown). For example, the diameter of lumen 166 may be within a range from approximately 0.004 inches to approximately 0.035 inches. In some examples, lumen 166 is configured to center cylindrical sub-assembly over one or more elongated conductors (not shown).

Outer insulative surface 168 may be configured to completely cover the entire substantially continuous interior surface of cylindrical conductive element 152, as illustrated in FIG. 5B, and provide support and electrical isolation to cylindrical conductive element 152. In the example of FIG. 5C, outer insulative surface 168 has cap 155 of insulative material on each end, which covers the ends of cylindrical conductive element 152. However, outer insulative surface 168 may not cover the ends of cylindrical conductive element 152 in gap 170, in some examples, because an uninsulated portion of an insulated elongated conductor (not shown) may extend above gap 170 to be attached (e.g., welded) to cylindrical conductive element 152 in gap 160.

Gap 170 allows an uninsulated portion of an insulated elongated conductor (not shown) to be attached (e.g., welded) to provide an electrical connection between cylindrical conductive element 152 and IMD 14 as described with respect to FIGS. 1A-1B. In some examples, gap 170 may have a width within a range from approximately 0.004 inches to approximately 0.025 inches. Protrusion 172 is a part of cylindrical insulative element 154, and provides stability to and alignment of insulative element 154 by preventing any movement of insulative element 154 relative to the cylindrical conductive element 152. In some examples, protrusion 172 of insulative element 154 extends through injection molding aperture 164 to be substantially congruent with the outer surface of cylindrical conductive element 152.

When lead 16 is assembled, there is a potential for the insulation on one or more of the elongated conductors to get damaged and, if liquid enters lead 16, could short two elongated conductors and cause a short or low impedance condition between circuits in lead 16. However, pre-molded cylindrical sub-assembly 150 may prevent one or more insulated elongated conductors from being damaged during assembly. Moreover, even if the one or more insulated elongated conductors were damaged prior to lead 16 being assembled, cylindrical insulative element 154 may prevent a short or low impedance condition between in lead 16.

Figure 6B:
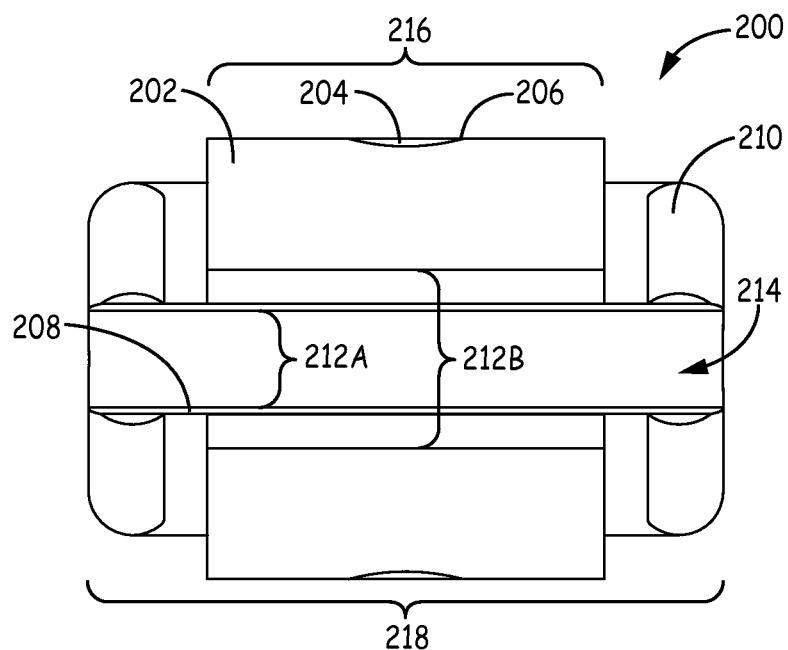
Figure 6C:
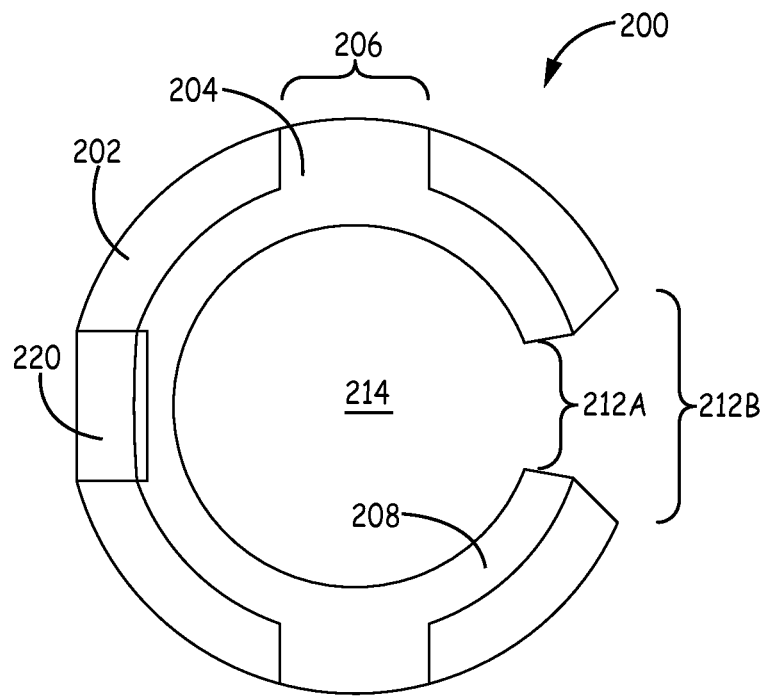
Figure 6D:
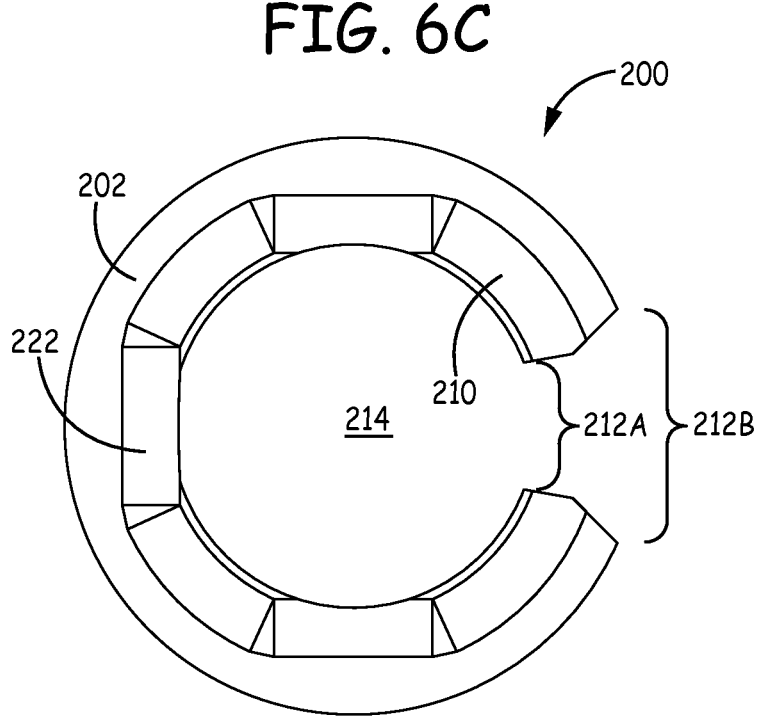

FIGS. 6A-6D are perspective and cross-sectional diagrams illustrating an example of a pre-molded cylindrical connector sub-assembly 200. In the example of FIG. 6A, pre-molded cylindrical connector sub-assembly 200 includes cylindrical conductive element 202, protrusion 204, injection molding aperture 206, cylindrical insulative element 208, insulative ridge 210, gap 212, and lumen 214. FIG. 6B is a top view diagram illustrating pre-molded cylindrical connector sub-assembly 200. FIG. 6C is a cross-sectional view diagram illustrating pre-molded cylindrical connector sub-assembly 200, the cross section taken along line B-B in FIG. 6A. FIG. 6D is an end view diagram illustrating pre-molded cylindrical connector sub-assembly 200.

Cylindrical conductive element 202 is formed by a conductive biocompatible material (e.g., metal). In the example of FIG. 6A, cylindrical conductive element 202 is formed to define a substantially continuous interior surface and a substantially continuous exterior surface, such that the substantially continuous interior surface allows for an insulative material to be injected into the interior of the cylindrical conductive element 202 to create pre-molded cylindrical connector sub-assembly 200. In the example of FIGS. 6A-6D, cylindrical conductive element 202 is a connector, e.g., connector 102, which connects IMD 14 to lead 16.

Protrusion 204 is a part of insulative element 208, and provides stability to and alignment of insulative element 208 by preventing movement of insulative element 208 relative to conductive element 202. In some examples, protrusion 204 extends through molding aperture 206 too be substantially congruent with the outer surface of cylindrical conductive element 202.

Injection molding aperture 206 is an aperture, which allows for an insulative material (e.g., a hardenable organic polymer material) to be injected into cylindrical conductive element 202 to form pre-molded cylindrical connector sub-assembly 200. In the example of FIG. 6B, two injection molding apertures 206 are respectively positioned on two sides of cylindrical conductive element 202 midway along the longitudinal axis and perpendicular to a vertical plane through gap 212. However, injection molding aperture 206 may be located anywhere that allows insulative material to be injected into cylindrical conductive element 202. In some examples, instead of or in addition to injection molding aperture 206, insulative material to form insulative element 208 may be introduced through lumen 214 or gap 212.

Insulative element 208 is formed by introducing an insulative material onto the interior surface of cylindrical conductive element 202, and can support and electrically isolate cylindrical conductive element 202 from an insulated elongated conductor (not shown). Insulative element 208 may be formed by injecting an insulative material into cylindrical conductive element 202, e.g., onto the substantially continuous inner surface of the conductive element, and processing the insulative material to define lumen 214 along a longitudinal axis and gap 212. For example, the insulative material may be processed by a mandrel to create lumen 214. In another example, the insulative material may be processed by trimming the insulative material, e.g., with a blade, mold tooling, or laser ablation, to create gap 212.

Insulative element 208, in some examples, may also extend beyond the outer surface at one or both ends of cylindrical conductive element 202 to form ridge 210. By placing ridge 210 at one or both ends of cylindrical conductive element 202, insulative element 208 may further electrically isolate cylindrical conductive element 202 from an insulated elongated element (not shown) and other cylindrical conductive elements. Insulative element 208 may also be of varying dimensions to improve the support and electrical isolation of cylindrical conductive element 202, and to minimize the potential of damaging one or more insulated elongated conductors during assembly of lead 16. In some examples, cylindrical insulative element 208 keeps pre-molded cylindrical connector sub-assembly 200 centered during injection molding of the overmold (e.g., overmolds 104 and 124 as described in FIGS. 3A-4B).

Insulative ridge 210 may be a ridge made of the same insulative material as insulative element 208, and may be created when insulative element 208 is injected into a mold. In some examples, insulative ridge 210 may provide improved shear force through the frictional force between insulative ridge 210 and an overmold (e.g., overmold 104 and 124, as described in FIGS. 3A-4B). Insulative ridge 210 may be made of insulative material, which may improve the AC impedance between pre-molded cylindrical connector sub-assembly 200 and the insulated elongated conductor. In some examples, insulative ridge 210 of insulative element 208 may minimize and/or eliminate the amount of contact between cylindrical conductive element 202 and the insulation of the elongated conductor. In some examples, the insulative material forming insulative ridge 210 and insulative element 208 may also have a low friction coefficient, which may minimize the friction between the insulation of the elongated conductor and the interior of the cylindrical connector sub-assembly 200, as the cylindrical connector sub-assembly is slid over the elongated conductor.

Gap 212 is a gap created by a combination of first gap 212B (FIG. 6B) in cylindrical conductive element 202 and second gap 212A (FIG. 6B) in cylindrical insulative element 208. In some examples, second gap 212A in insulative element 208 is created by trimming the insulative material, e.g., with a blade, mold tooling, or laser ablation, after the insulative material has been hardened. In other examples, second gap 212A in cylindrical insulative element 208 is created by removing the insulative material before the insulative material has been hardened. In some examples, gap 212 may, as illustrated in FIGS. 6A and 6B, be a longitudinal channel. Gap 212 may allow access to elongated conductors 108, 128 while the conductors are positioned within lumen 214 during assembly of lead 16, to allow electrical connection of one of the conductors to the cylindrical conductive element 202, e.g., via resistance welding. Gap 212 may facilitate such electrical connection without the need to unwind each conductor, e.g., each filer. In some examples, each of a plurality of pre-molded cylindrical sub-assemblies 200 may be positioned longitudinally along an elongated conductor, and gaps 212 may facilitate collective electrical connection of the cylindrical conductive elements 202 in this arrangement, rather than individual positioning and electrical connection as a two-step process repeated for each of the pre-molded cylindrical sub-assemblies 200.

Lumen 214 is an aperture along a longitudinal axis of pre-molded cylindrical sub-assembly 200, and is configured to receive an insulated elongated conductor (not shown). In some examples, lumen 214 may be used to center cylindrical conductive 202 along lead 16. Lumen 214 of insulative element 208 may be created by inserting a mandrel into a lumen (now shown) of cylindrical conductive element 202 during forming of insulative element 208 onto the interior surface of cylindrical conductive element 202 and over the mandrel.

FIG. 6B is a top view diagram illustrating cylindrical connector sub-assembly 200. A first length 216 of cylindrical conductive element 202 may be within a range from approximately 0.020 inches to approximately 0.150 inches. A second length 218 of cylindrical insulative element 208 may be within a range from about 0.020 inches to approximately 0.150 inches. As illustrated in FIG. 6B, second length 218 of insulative element 208 may be greater than first length 216 of cylindrical conductive element 202. In other words, one or more ends of insulative element 208 may protrude beyond one or more corresponding ends of cylindrical conductive element 202. A first gap 212B of cylindrical conductive element 202 may be within a range of widths from approximately 0.004 inches to approximately 0.025 inches. A second gap 212A of insulative element 208 may be within a range of widths from approximately 0.004 inches to approximately 0.025 inches. The widths of gaps 212A and 212B may be different, e.g., gap 212A of insulative element 208 may be narrower than gap 212B of conductive element 202.

As illustrated in FIG. 6C, insulative element 208 may include a recess 220. Recess 220 may correspond to a hole formed during formation of cylindrical conductive element 202, e.g., by a pin during molding of the cylindrical conductive element 202. The hole in cylindrical conductive element 202 may allow for alignment with a pin in a mold used during introduction of insulative material to form insulative element 208. Flat surfaces, e.g., flat surface 222 in FIG. 6D, may be formed by features of conductive element 202 and/or a mold that facilitate flow of insulative material around the insulative element and/or conductive element during molding of the insulative element, and prevent exposure of the insulative element to the outer diameter of the assembly.

Figure 7B:
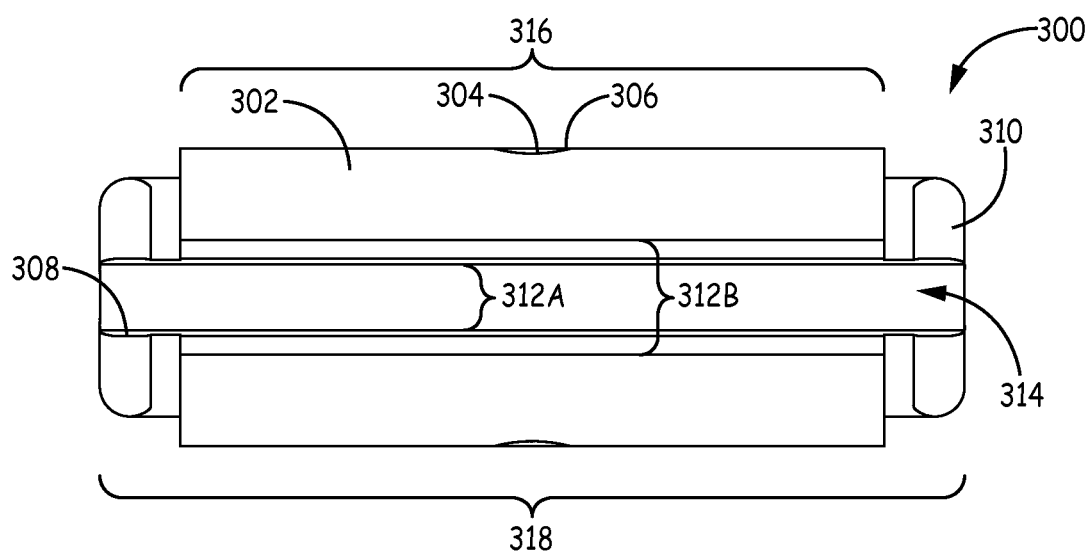
Figure 7C:
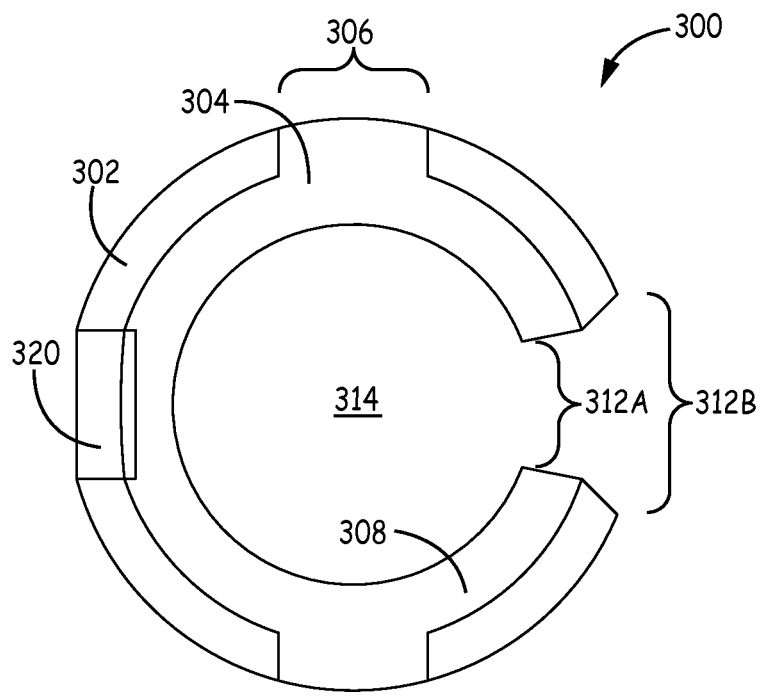
Figure 7D:
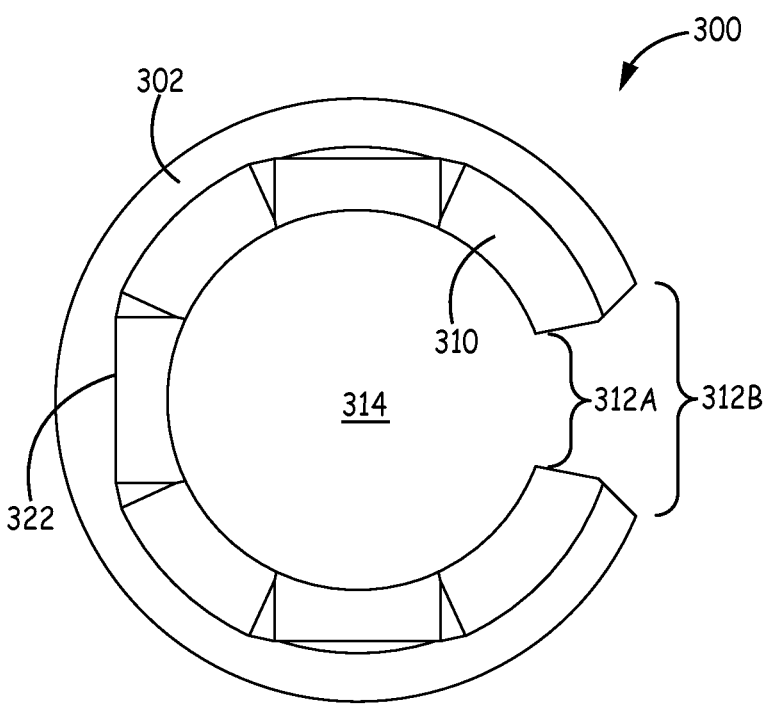

FIGS. 7A-7D are perspective and cross-sectional diagrams illustrating an example of pre-molded cylindrical electrode sub-assembly 300. In the example of FIG. 7A, pre-molded cylindrical electrode sub-assembly 300 includes cylindrical conductive element 302, protrusion 304, injection molding aperture 306, cylindrical insulative element 308, insulative ridge 310, gap 312, and lumen 314, FIG. 7B is a top view diagram illustrating pre-molded cylindrical electrode sub-assembly 300. FIG. 7C is a cross-sectional view diagram illustrating pre-molded cylindrical electrode sub-assembly 300, the cross section taken along line C-C in FIG. 7A. FIG. 7D is an end view diagram illustrating pre-molded cylindrical electrode sub-assembly 300.

Cylindrical conductive element 302 is formed by a conductive biocompatible material (e.g., metal). In the example of FIG. 7A, cylindrical conductive element 302 is formed to define a substantially continuous interior surface and a substantially continuous exterior surface, such that the substantially continuous interior surface allows for an insulative material to be injected into the interior of the cylindrical conductive element 302 to create pre-molded cylindrical electrode sub-assembly 300. In the example of FIGS. 7A-7D, cylindrical conductive element 302 is an electrode, e.g., electrode 122, which electrically connects lead 16 to tissues or organs of patient 12.

Protrusion 304 is a part of insulative element 308, and provides stability to and alignment of insulative element 308 by preventing movement of insulative element 308 relative to conductive element 302. In some examples, protrusion 304 extends through molding aperture 306 too be substantially congruent with the outer surface of cylindrical conductive element 302.

Injection molding aperture 306 is an aperture, which allows for an insulative material (e.g., a hardenable organic polymer material) to be injected into cylindrical conductive element 302 to form pre-molded cylindrical electrode sub-assembly 300. In the example of FIG. 7B, two injection molding apertures 306 are respectively positioned on two sides of cylindrical conductive element 302 midway along the longitudinal axis and perpendicular to a vertical plane through gap 312. However, injection molding aperture 306 may be located anywhere that allows insulative material to be injected into cylindrical conductive element 302. In some examples, instead of or in addition to injection molding aperture 306, insulative material to form insulative element 308 may be introduced through lumen 314 or gap 312.

Insulative element 308 is formed by introducing an insulative material onto the interior surface of cylindrical conductive element 302, and can support and electrically isolate cylindrical conductive element 302 from an insulated elongated conductor (not shown). Insulative element 308 may be formed by injecting an insulative material into cylindrical conductive element 302, e.g., onto the substantially continuous inner surface of the conductive element, and processing the insulative material to define lumen 314 along a longitudinal axis and gap 312. For example, the insulative material may be processed by a mandrel to create lumen 314. In another example, the insulative material may be processed by trimming the insulative material, e.g., with a blade, mold tooling, or laser ablation, to create gap 312.

Insulative element 308, in some examples, may also extend beyond the outer surface at one or both ends of cylindrical conductive element 302 to form ridge 310. By placing ridge 310 at one or both ends of cylindrical conductive element 302, insulative element 308 may further electrically isolate cylindrical conductive element 302 from an insulated elongated element (not shown) and other cylindrical conductive elements. Insulative element 308 may also be of varying dimensions to improve the support and electrical isolation of cylindrical conductive element 302, and to minimize the potential of damaging one or more insulated elongated conductors during assembly of lead 16. In some examples, cylindrical insulative element 308 keeps pre-molded cylindrical electrode sub-assembly 300 centered during injection molding of the overmold (e.g., overmolds 104 and 124 as described in FIGS. 3A-4B).

Insulative ridge 310 may be a ridge made of the same insulative material as insulative element 308, and may be created when insulative element 308 is injected into a mold. In some examples, insulative ridge 310 may provide improved shear force through the frictional force between insulative ridge 310 and an overmold (e.g., overmold 104 and 124, as described in FIGS. 3A-4B). Insulative ridge 310 may be made of insulative material, which may improve the AC impedance between pre-molded cylindrical electrode sub-assembly 300 and the insulated elongated conductor. In some examples, insulative ridge 310 of insulative element 308 may minimize and/or eliminate the amount of contact between cylindrical conductive element 302 and the insulation of the elongated conductor. In some examples, the insulative material forming insulative ridge 310 and insulative element 308 may also have a low friction coefficient, which may minimize the friction between the insulation of the elongated conductor and the interior of the cylindrical electrode sub-assembly 300, as the cylindrical electrode sub-assembly is slid over the elongated conductor.

Gap 312 is a gap created by a combination of first gap 312B (FIG. 7B) in cylindrical conductive element 302 and second gap 312A (FIG. 7B) in cylindrical insulative element 308. In some examples, second gap 312A in insulative element 308 is created by trimming the insulative material, e.g., with a blade, mold tooling, or laser ablation, after the insulative material has been hardened. In other examples, second gap 312A in cylindrical insulative element 308 is created by removing the insulative material before the insulative material has been hardened. In some examples, gap 312 may, as illustrated in FIGS. 7A and 7B, be a longitudinal channel. Gap 312 may allow access to elongated conductors 108, 128 while the conductors are positioned within lumen 314 during assembly of lead 16, to allow electrical connection of one of the conductors to the cylindrical conductive element 302, e.g., via resistance welding. Gap 312 may facilitate such electrical connection without the need to unwind each conductor, e.g., each filer. In some examples, each of a plurality of pre-molded cylindrical sub-assemblies 300 may be positioned longitudinally along an elongated conductor, and gaps 312 may facilitate collective electrical connection of the cylindrical conductive elements 302 in this arrangement, rather than individual positioning and electrical connection as a two-step process repeated for each of the pre-molded cylindrical sub-assemblies 300.

Lumen 314 is an aperture along a longitudinal axis of pre-molded cylindrical sub-assembly 300, and is configured to receive an insulated elongated conductor (not shown). In some examples, lumen 314 may be used to center cylindrical conductive 302 along lead 16. Lumen 314 of insulative element 308 may be created by inserting a mandrel into a lumen (now shown) of cylindrical conductive element 302 during forming of insulative element 308 onto the interior surface of cylindrical conductive element 302 and over the mandrel.

FIG. 7B is a top view diagram illustrating cylindrical electrode sub-assembly 300. A first length 316 of cylindrical conductive element 302 may be within a range from approximately 0.020 inches to approximately 0.150 inches. A second length 318 of cylindrical insulative element 308 may be within a range from approximately 0.020 inches to approximately 0.150 inches. As illustrated in FIG. 7B, second length 318 of insulative element 308 may be greater than first length 316 of cylindrical conductive element 302. In other words, one or more ends of insulative element 308 may protrude beyond one or more corresponding ends of cylindrical conductive element 302. A first gap 312B of cylindrical conductive element 302 may be within a range of widths from approximately 0.004 inches to approximately 0.025 inches. A second gap 312A of insulative element 208 may be within a range of widths from approximately 0.004 inches to approximately 0.025 inches. The widths of gaps 312A and 312B may be different, e.g., gap 312A of insulative element 308 may be narrower than gap 312B of conductive element 302.

As illustrated in FIG. 7C, insulative element 308 may include a recess 320. Recess 320 may correspond to a hole formed during formation of cylindrical conductive element 302, e.g., by a pin during molding of the cylindrical conductive element 302. The hole in cylindrical conductive element 302 may allow for alignment with a pin in a mold used during introduction of insulative material to form insulative element 308. Flat surfaces, e.g., flat surface 322 of insulative element 310 in FIG. 7D, may be formed by features of conductive element 302 and/or a mold that facilitate flow of insulative material around the insulative element and/or conductive element during molding of the insulative element, and prevent exposure of the insulative element to the outer diameter of the assembly.

Figure 8A:
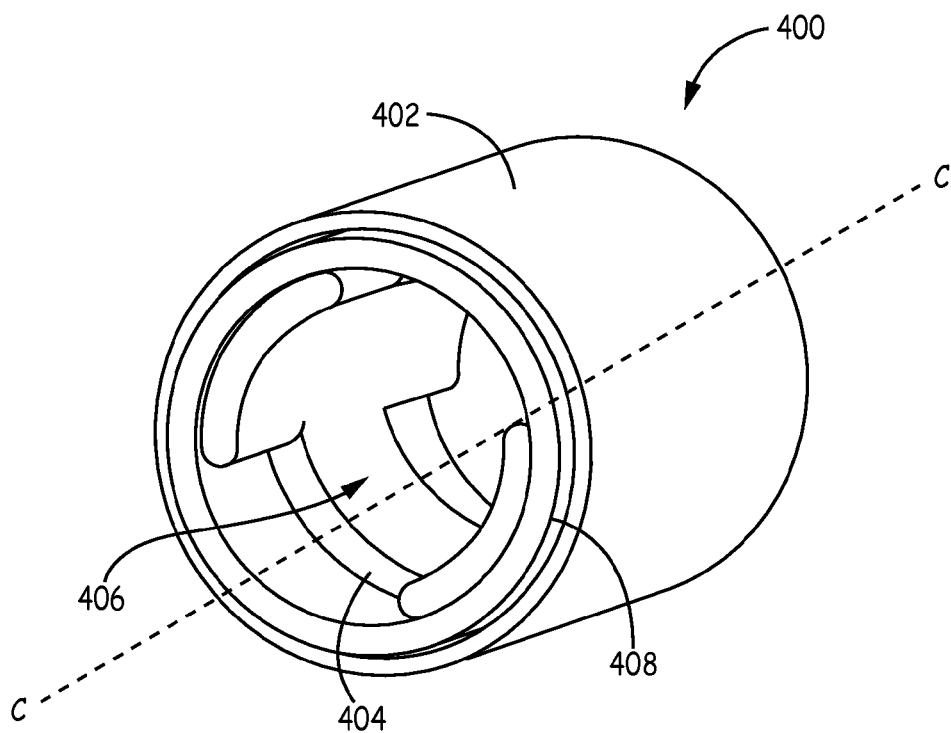
FIGS. 8A-8C are perspective and cross-sectional diagrams illustrating an example of a pre-molded cylindrical electrode sub-assembly configured to be included at a distal end of an implantable medical lead for deep brain stimulation (DBS).
Figure 8B:
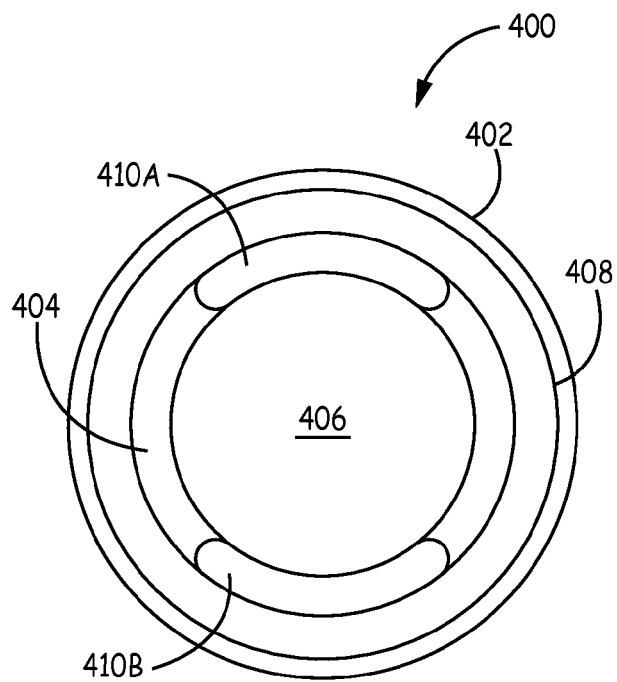
Figure 8C:
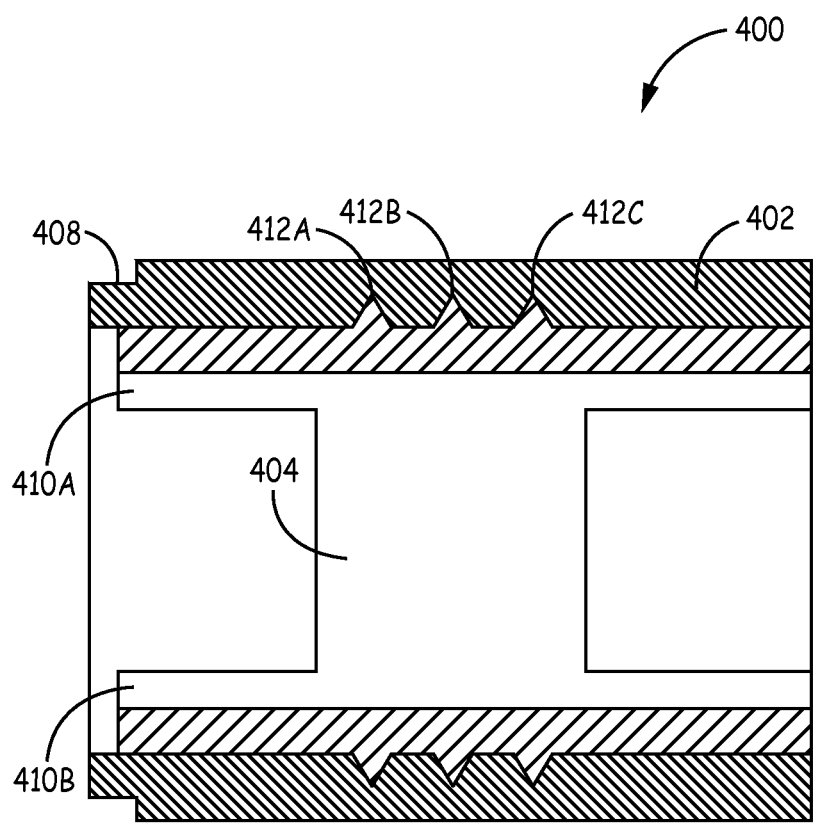

FIGS. 8A-8C are perspective and cross-sectional diagrams illustrating an example of a pre-molded cylindrical sub-assembly 400, which may be configured to be included at a distal end of an implantable medical lead for deep brain stimulation (DBS). In the examples of FIGS. 8A-8C, pre-molded cylindrical electrode sub-assembly 400 includes cylindrical conductive element 402, insulative element 404, and lumen 406. FIG. 8C illustrates a cross-section of pre-molded cylindrical sub-assembly 400 taken along line C-C in FIG. 8A.

In contrast to the pre-molded cylindrical electrode sub-assembly 300 of FIGS. 7A-7D, pre-molded cylindrical electrode sub-assembly 400 of FIGS. 8A-8C does not include gap 312 in conductive element 402. In some examples, full cylindrical rings may be needed for connections using a set screw, and slotted rings (e.g., with gap 312) may be used for connections using spring contacts. In some examples, both designs may create acceptable fields for stimulation. However, full rings, such as that provided by conductive element 402, may provide better stimulation for therapies like DBS due to the sensitivity of stimulating a very localized point within the brain.

Additionally, pre-molded cylindrical electrode sub-assembly 400 has other features that differ from pre-molded cylindrical electrode sub-assembly 300 of FIGS. 7A-7D. In the example of FIGS. 8A-8C, pre-molded cylindrical electrode sub-assembly 400 includes flange 408 of cylindrical conductive element 402. In some examples, flange 408 may increase tensile strength through a better bonding connection with an overmold material. In some examples, flange 408 may be similar to insulative ridge 310.

Additionally, as illustrated in FIGS. 8B and 8C, insulative element 404 may not extend the entire longitudinal length of cylindrical conductive element 402 around all, or a portion of, the circumference of the conductive element. In such examples, insulative element 404 may include portions 410A and 410B (collectively, "portions 410") that extend substantially the entire length of cylindrical conductive element 402. In some examples, portions 410 may extend beyond one or both ends, e.g., greater than the longitudinal length, of cylindrical conductive element 402. The illustrated number, shape and dimensions of portions 410 are one example, and other example portions 410 may have other numbers, shapes, or dimensions. In some examples, portions 410 may be similar to insulative ridge 310, and may further improve the tensile strength through a better bonding connection with an overmold material. In some examples, longitudinal portions 410 may provide an increase in stability (e.g., by preventing sub-assembly 400 from twisting on lead 16) through a better bonding connection with the overmold material. In some examples, longitudinal portions 410 may have a different melting point than the overmold material, which may provide a better bonding connection between pre-molded cylindrical electrode sub-assembly 400 and longitudinal portions 410.

Additionally, as illustrated in FIG. 8C, cylindrical conductive element 402 of sub-assembly 400 may include a plurality of circumferential grooves 412A-412C (collectively, "grooves 412"). In such examples, cylindrical conductive element may not include an injection molding aperture, e.g., aperture 164, and insulative material to form insulative element 404 may be introduced through lumen 406 of cylindrical conductive element 402. Protrusion of the insulative material into grooves 412 may provide stability to and alignment of insulative element 404 by preventing any movement of insulative element 404 relative to the cylindrical conductive element 402. The illustrated number, shapes, and locations of grooves 412 are one example, and other conductive elements may have other numbers, shapes, and/or locations of grooves 412.

Figure 9:
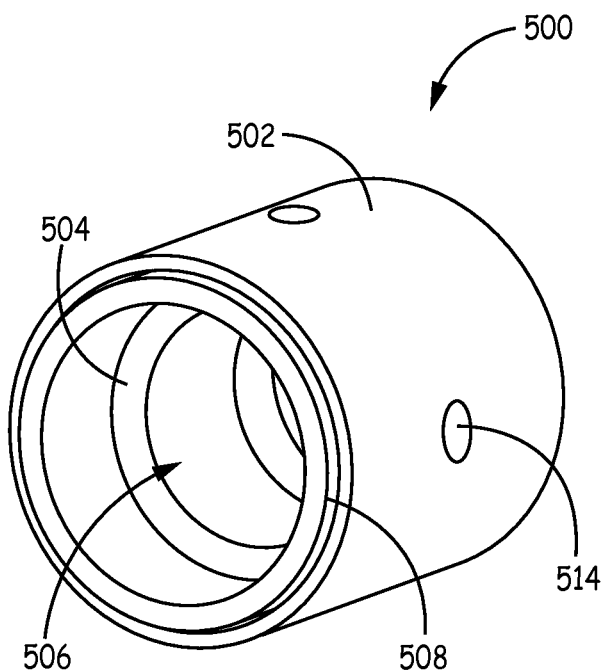
FIG. 9 is a perspective diagram illustrating another example of a pre-molded cylindrical electrode sub-assembly configured to be included at a distal end of an implantable medical lead for deep brain stimulation (DBS).

FIG. 9 is a perspective diagram illustrating another example of a pre-molded cylindrical electrode sub-assembly 500, which may be configured to be included at a distal end of an implantable medical lead for deep brain stimulation (DBS). Like pre-molded cylindrical electrode sub-assembly 400 of FIGS. 8A-8C, pre-molded cylindrical electrode sub-assembly 500 includes a conductive element 502, insulative element 504, lumen 506, and flange 508. Insulative element 504 does not include longitudinal portions that extend to the ends of conductive element 502. Additionally, cylindrical conductive element 502 includes injection molding apertures 514, which allows for an insulative material to be injected into cylindrical conductive element 502 and onto the interior surface of cylindrical conductive element 502 to form pre-molded cylindrical sub-assembly 500. In such examples, cylindrical conductive element 502 may not include grooves 412 (FIG. 8C).

Figure 10:
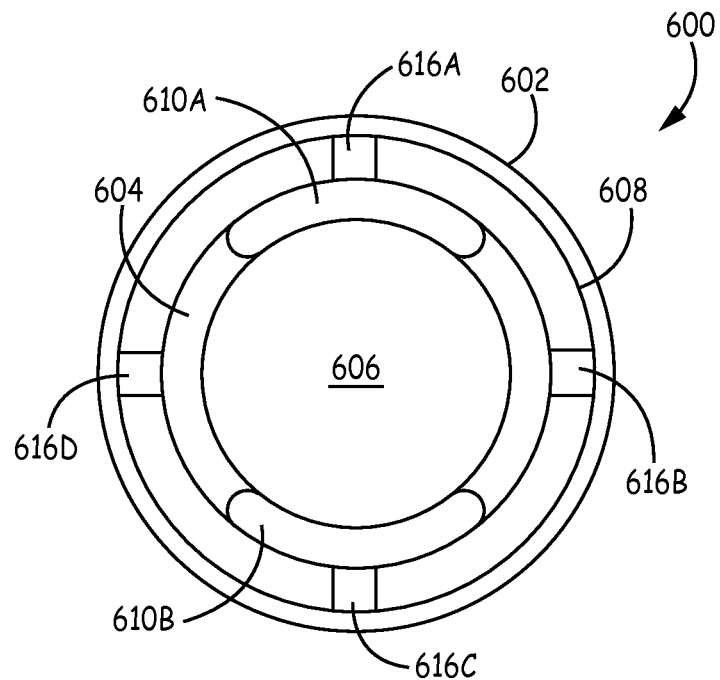
FIG. 10 is an end-view diagram illustrating another example of a pre-molded cylindrical electrode sub-assembly configured to be included at a distal end of an implantable medical lead for deep brain stimulation (DBS).

FIG. 10 is an end-view diagram illustrating another example of a pre-molded cylindrical electrode sub-assembly 600, which may be configured to be included at a distal end of an implantable medical lead for deep brain stimulation (DBS). Like pre-molded cylindrical electrode sub-assembly 400 of FIGS. 8A-8C, pre-molded cylindrical electrode sub-assembly 600 includes a cylindrical conductive element 602, insulative element 604, lumen 606, and flange 608. Additionally, like pre-molded cylindrical electrode sub-assembly 400 of FIGS. 8A-8C, insulative element 604 includes longitudinal portions 610A and 610B. Additionally, flange 608 of cylindrical conductive element 602 further defines slots 616A-616D (collectively "slots 616"). In some examples, slots 616 of flange 608 may further improve the tensile strength through a better bonding connection with an overmold material. In some examples, slots 616 may provide an increase in stability (e.g., slots 616 prevent sub-assembly 600 from twisting on the lead) through a better bonding connection with the overmold material.

Figure 11:
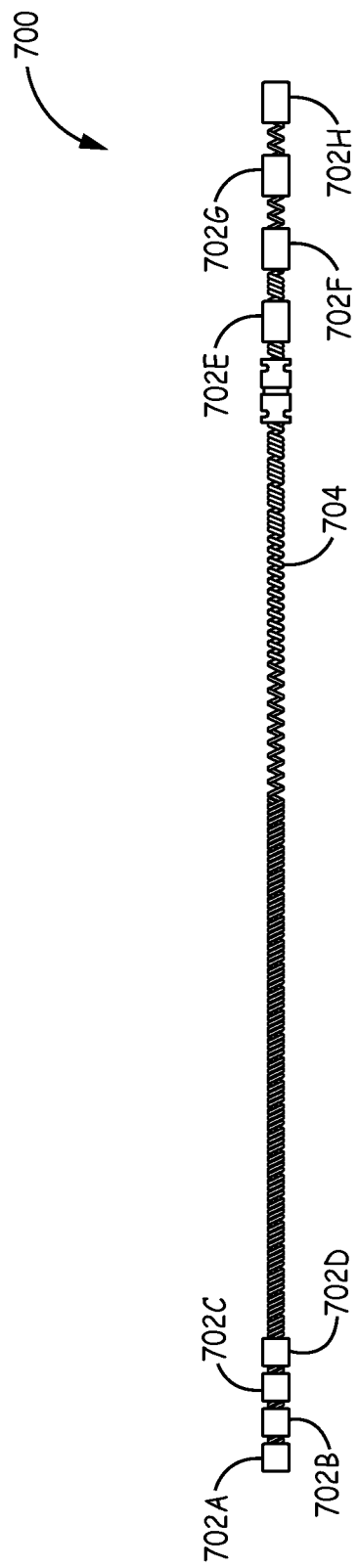
FIG. 11 is a conceptual diagram illustrating an example of an implantable medical lead, including a plurality of pre-molded cylindrical sub-assemblies, before an application of an overmold.

FIG. 11 is a conceptual diagram illustrating an example of an implantable medical lead 700, including a plurality of pre-molded cylindrical sub-assemblies 702A-702H (collectively, "pre-molded cylindrical sub-assemblies 702"), before an application of an overmold. FIG. 11 also illustrates one or more elongated conductors 704 inserted through the lumens (not shown) of pre-molded cylindrical sub-assemblies 702. Pre-molded cylindrical sub-assemblies 702 are positioned at respective locations along the longitudinal axis of elongated conductors 704. The locations of pre-molded cylindrical sub-assemblies 702 may be selected based on the intended functionality of the cylindrical conductive elements of the pre-molded cylindrical sub-assemblies 702A-702D, as connectors 102 at a proximal end of the lead, or sub-assemblies 702E-702H as electrodes 122 at a distal end of the lead.

As discussed above, elongated conductors 704 may be a plurality of coiled conductors arranged in a co-radial, helical configuration, and within an insulator. With pre-molded cylindrical sub-assemblies 702 positioned as shown in FIG. 11, respective ones of elongated conductors 704 may be accessed at the end of the pre-molded cylindrical sub-assemblies 702, and electrically connected to respective ones of cylindrical conductive elements of the of pre-molded cylindrical sub-assemblies 702. Lead 700, including pre-molded cylindrical sub-assemblies 702 and elongated conductors 704 arranged as shown in FIG. 11, and with the elongated conductors connected to respective ones of cylindrical conductive elements of the of pre-molded cylindrical sub-assemblies 702, may be overmolded. For example, lead 700, including pre-molded cylindrical sub-assemblies 702 and elongated conductors 704 arranged as shown in FIG. 11, and with the elongated conductors connected to respective ones of cylindrical conductive elements of the of pre-molded cylindrical sub-assemblies 702 may be placed into a mold for injection molding of an overmold.

In some examples, an overmold is a hardenable organic polymeric material, which is injected into a mold containing lead 700, and fills in the interstices of pre-molded cylindrical sub-assemblies 702. In some examples, after hardening the organic polymeric material to create an overmold, a portion of the overmold may be trimmed and/or removed to expose pre-molded cylindrical sub-assemblies 702, such that pre-molded cylindrical sub-assemblies 702 may have an electrical connection with IMD 14 and/or with tissue and/or organs. The overmold may expose the conductive elements of pre-molded cylindrical sub-assemblies 702 while providing support and isolation between pre-molded cylindrical sub-assemblies 702, and protecting the interior of lead 700, e.g., conductors 704, from external conditions.

Figure 12:
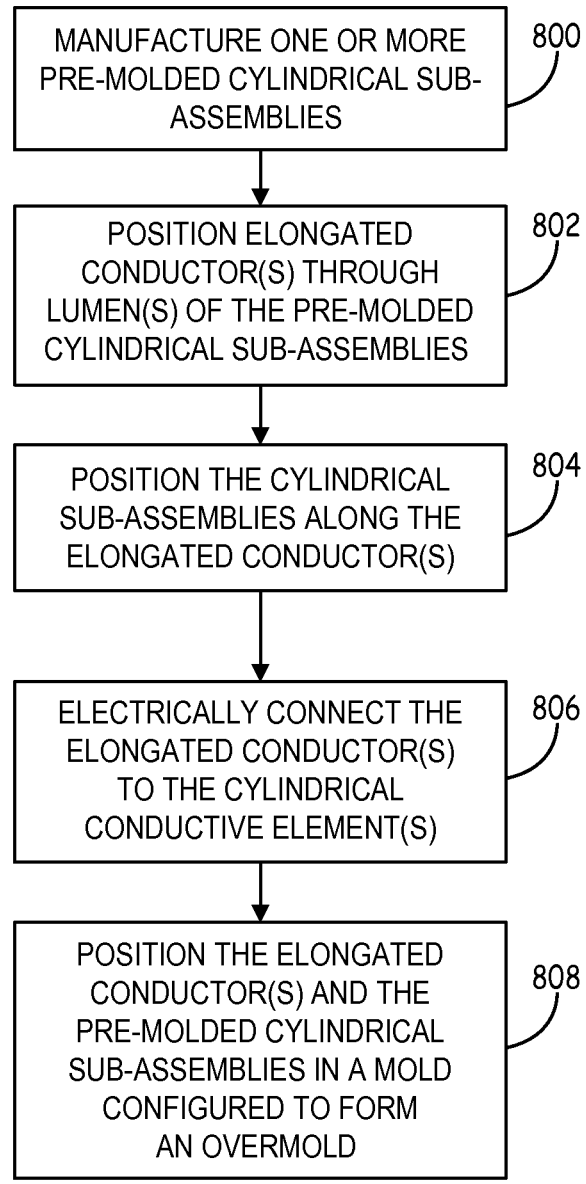
FIG. 12 is a flow diagram illustrating an example method of manufacturing an implantable medical lead that includes at least one pre-molded cylindrical sub-assembly.

FIG. 12 is a flow diagram illustrating an example method of manufacturing an implantable medical lead that includes at least one pre-molded cylindrical sub-assembly. In the example of FIG. 12, the at least one pre-molded cylindrical sub-assembly may be either a connector at a proximal end (e.g., connector 102 at proximal end 20 as described in FIGS. 3A-3B) or an electrode at a distal end (e.g., electrode 122 at distal end 22 as described in FIG. 4A-4B).

According to the example method of FIG. 12, one or more pre-molded cylindrical sub-assemblies, e.g., any of the pre-molded cylindrical sub-assemblies described herein, are manufactured to include a cylindrical conductive element with substantially continuous interior and exterior surfaces, and an insulative element formed on the interior surface, as described herein and in greater detail below with respect to FIG. 13 (800). The one or more elongated conductors are positioned through the lumens of the one or more pre-molded cylindrical sub-assemblies, e.g., the one or more pre-molded cylindrical sub-assemblies are assembled (e.g., slid) onto the one or more elongated conductors (e.g., coil conductors) at a distal or proximal end of lead 16 (802). As described herein, the one or more pre-molded cylindrical sub-assemblies are configured to receive at least one insulated elongated conductor through the lumen of the one or more pre-molded cylindrical sub-assemblies. After receiving the one or more elongated conductors, the one or more pre-molded cylindrical sub-assemblies are positioned along the elongated conductors at a distal or proximal end of lead 16 at desired positions for their function as connectors or electrodes (804).

After the one or more pre-molded cylindrical sub-assemblies are positioned at either a distal or a proximal end of the lead, an uninsulated portion of a substantially insulated elongated conductor (e.g., individual coil filer) is electrically connected (e.g., welding or adhesion) to the conductive element of a pre-molded cylindrical sub-assembly creating a lead body assembly at the distal or proximal end of the lead (806). In some examples, a longitudinal channel (e.g., gap 158, 212, 312 as described in FIGS. 5A, 6A, 7A) on the one or more pre-molded cylindrical sub-assemblies allows for resistance welding, and there is no need to unwind each filer. After the one or more pre-molded cylindrical sub-assemblies are attached, then the lead body assembly is placed in a mold and receives injection molding for final potting and form factor (e.g., forming overmold 104, 124 as described in FIGS. 3A-4B) (808).

In some examples, an insulative element of the one or more pre-molded cylindrical sub-assemblies helps keep the one or more pre-molded cylindrical sub-assemblies centered during injection molding of the overmold. In some examples, the insulation on the one or more insulated elongated conductors may be damaged during lead assembly. In some examples, the insulation on the one or more insulated elongated conductors may be defective from improper manufacturing. If liquid enters lead 16 with two or more damaged elongated conductors, the damaged elongated conductors may short or may cause a low impedance condition. In other words, a pre-molded cylindrical sub-assembly aids in final potting and isolation, which decreases the likelihood of a short or low impedance condition between circuits in the lead. In some examples, using a pre-molded cylindrical sub-assembly may minimize the potential for damaging the insulated elongated conductors during assembly, and may minimize the likelihood of low impedance conditions.

In general, when overmolding leads that include electrodes and connectors without an insulative element to form a pre-molded cylindrical assembly according to this disclosure, a void may be left after a first shot of the injection molding, and a second shot is required after the first shot to fill the void. In contrast, pre-molded cylindrical sub-assemblies according to this disclosure may require only a single shot of injection molding to form an overmold after the one or more pre-molded cylindrical sub-assemblies are assembled on the lead. One advantage that may result from use of a pre-molded cylindrical sub-assembly according to the techniques of this disclosure is the protection of the elongated conductors during lead assembly and the maximization of the distance from the elongated conductors to the conductive element due to better centering of the elongated conductors within the pre-molded cylindrical sub-assemblies. Another advantage that may result from use of a pre-molded cylindrical sub-assembly according to the techniques of this disclosure is improved AC impedance performance, e.g., due to avoiding damage to the elongated conductors or their insulation during lead assembly.

Another advantage that may result from use a pre-molded cylindrical sub-assembly according to the techniques of this disclosure is that adhesive or separate reflowing of the insulative material on the interior of the pre-molded cylindrical sub-assembly may not be necessary to achieve desired mechanical properties of the lead, such as tensile strength. Another advantage that may result from use of a pre-molded cylindrical sub-assembly according to the techniques of this disclosure is that the insulation layer may be increased, e.g., due to the presence and bonding of the insulation of the elongated conductors and the insulative layer of the pre-molded cylindrical sub-assembly, which may provide increased tensile strength and an improved hipot yield, e.g., improved performance under high electrical potential conditions. Another advantage that may result from use of a pre-molded cylindrical sub-assembly according to the techniques of this disclosure is potential for improved straightness of the proximal and distal ends of the implantable medical lead.

Figure 13:
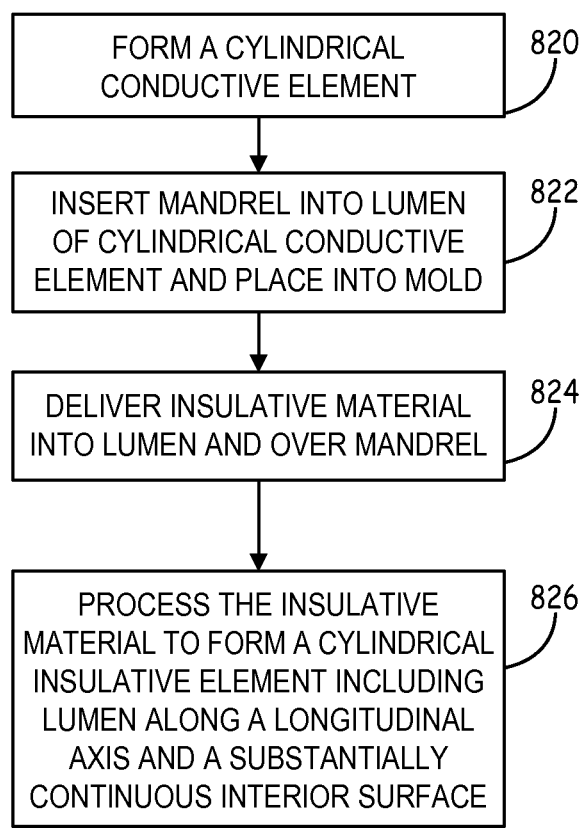
FIG. 13 is a flow diagram illustrating an example method of manufacturing a pre-molded cylindrical sub-assembly.

FIG. 13 is a flow diagram illustrating an example method of manufacturing a pre-molded cylindrical sub-assembly. In the example of FIG. 13, the pre-molded cylindrical sub-assembly may be either a connector at a proximal end (e.g., connector 102 at proximal end 20 as described in FIGS. 3A-3B) and/or an electrode at a distal end (e.g., electrode 122 at distal end 22 as described in FIG. 4A-4B).

In general, a pre-molded cylindrical sub-assembly is manufactured by forming a cylindrical conductive element to include a substantially continuous interior surface and a substantially continuous exterior surface (820). After forming the cylindrical conductive element, the cylindrical conductive element is placed into a mold with a mandrel inserted into a lumen of the cylindrical conductive element (822). The example method of FIG. 13 further including delivering, e.g., injecting, an insulative material (e.g., a hardenable organic polymer material) into the lumen of the cylindrical conductive element, and over the mandrel (824). After the insulative material is introduced and hardened, the insulative material may be processed to define a lumen along a longitudinal axis and a substantially continuous interior of an insulative element, e.g. cylindrical insulative element (826).

In some examples, the substantially continuous interior and exterior surface of the cylindrical conductive element includes a first gap (e.g., gap 212B, 312B as described in FIGS. 6B and 7B), which may be part of a single longitudinal channel. In some examples, the substantially continuous interior surface of the cylindrical insulative element includes a second gap (e.g., gap 212A and 312A as described in FIGS. 6A and 7A), which may be part of a single longitudinal channel (e.g., gap 158, 212, and 312 as described in FIGS. 5A, 6A, and 7A). In circumstances where the insulation of the elongated conductor may be easily damaged, the hardenable organic polymer material may have a low friction coefficient to limit amount of friction applied to the insulation of the elongated conductor as the pre-molded cylindrical sub-assembly is slid over the elongated conductor.

Various examples of the disclosure have been described. These and other examples are within the scope of the following claims.

The invention claimed is:

1. An implantable medical lead configured to conduct an electrical signal between an implantable medical device and tissue of a patient, the implantable medical lead comprising:
   a plurality of elongated conductors;
   a proximal end comprising a plurality of connectors, each of the connectors electrically connected to one of the conductors, wherein each of the connectors is configured to electrically connect the one of the conductors to the implantable medical device;
   a distal end comprising a plurality of electrodes, each of the electrodes electrically connected to one of the conductors, wherein each of the electrodes is configured to electrically connect the one of the conductors to the tissue; and
   a plurality of pre-molded cylindrical sub-assemblies, each of the sub-assemblies comprising:
      a cylindrical conductive element formed from a conductive material to define a substantially continuous interior surface and a substantially continuous exterior surface, wherein the cylindrical conductive element is either one of the plurality of connectors or one of the plurality of electrodes; and
      an insulative element formed from an insulative material molded onto the interior surface of the cylindrical conductive element, wherein an interior surface of the insulative element defines a lumen of the pre-molded cylindrical sub-assembly configured to receive at least one of the elongated conductors of the implantable medical lead, and the cylindrical conductive element is configured to be electrically connected to one of the elongated conductors within the lumen;
   wherein the lumen defined by at least one insulative element is configured to receive more than one of the elongated conductors.

2. The implantable medical lead of claim 1, wherein the insulative material of the insulative element comprises a hardenable organic polymeric material selected from the group consisting of polyurethanes, polyurethanes with surface-modifying end groups, polyurethane silicone block copolymers, silicones, fluoropolymers, fluoroelastomers, polyethylenes, and polyesters.

3. The implantable medical lead of claim 1, further comprising an overmold adjacent the plurality of pre-molded cylindrical sub-assemblies and over the plurality of elongated conductors.

4. The implantable medical lead of claim 3, wherein the overmold comprises a hardenable organic polymeric material selected from the group consisting of polyurethanes, polyurethanes with surface-modifying end groups, polyurethane silicone block copolymers, silicones, fluoropolymers, fluoroelastomers, polyethylenes, and polyesters.

5. The implantable medical lead of claim 3, wherein the insulative element is configured to center the at least one of the elongated conductors within the lumen of the pre-molded cylindrical sub-assembly during overmolding of the overmold adjacent the plurality of pre-molded cylindrical sub-assemblies and over the plurality of elongated conductors.

6. The implantable medical lead of claim 3, wherein the insulative element is configured to bond to the overmold during overmolding of the overmold adjacent the plurality of pre-molded cylindrical sub-assemblies and over the plurality of elongated conductors.

7. The implantable medical lead of claim 1, wherein the plurality of elongated conductors comprise one or more elongated conductors within insulation, and wherein the insulative element is configured to prevent contact between the interior surface of the cylindrical conductive element and insulation of the one or more elongated conductors.

8. The implantable medical lead of claim 1, wherein each of the connectors and the electrodes of the lead is the cylindrical conductive element of a respective one of the pre-molded cylindrical sub-assemblies.

9. The implantable medical lead of claim 1, wherein the insulative element comprises a substantially cylindrical insulative element molded onto substantially all of the interior surface of the substantially cylindrical conductive element, and wherein the substantially cylindrical insulative element defines a substantially continuous interior surface that defines the lumen of the pre-molded cylindrical sub-assembly.

10. A pre-molded cylindrical sub-assembly for inclusion in an implantable medical lead configured to conduct an electrical signal between an implantable medical device and tissue of a patient, wherein the pre-molded cylindrical sub-assembly comprises:
 a cylindrical conductive element formed from a conductive material to define a substantially continuous interior surface and a substantially continuous exterior surface; and
 an insulative element formed from an insulative material molded onto the interior surface of the cylindrical conductive element, wherein an interior surface of the insulative element defines a lumen of the pre-molded cylindrical sub-assembly configured to receive a plurality of elongated conductors of the implantable medical lead, and the cylindrical conductive element is configured to be electrically connected to one of the elongated conductors within the lumen.

11. The pre-molded cylindrical sub-assembly of claim 10, wherein the cylindrical conductive element comprises an electrode configured to deliver electrical stimulation from the elongated conductor to the tissue of the patient.

12. The pre-molded cylindrical sub-assembly of claim 11, wherein the cylindrical conductive element comprises a ring electrode.

13. The pre-molded cylindrical sub-assembly of claim 10, wherein the cylindrical conductive element comprises a connector configured to electrically connect the implantable medical device to the elongated conductor.

14. The pre-molded cylindrical sub-assembly of claim 10, wherein the insulative material of the insulative element comprises a hardenable organic polymeric material selected from the group consisting of polyurethanes, polyurethanes with surface-modifying end groups, polyurethane silicone block copolymers, silicones, fluoropolymers, fluoroelastomers, polyethylenes, and polyesters.

15. The pre-molded cylindrical sub-assembly of claim 10, wherein the insulative element is configured to center the plurality of elongated conductors within the lumen of the pre-molded cylindrical sub-assembly during overmolding of an overmold adjacent the pre-molded cylindrical sub-assembly and over the plurality of elongated conductors.

16. The pre-molded cylindrical sub-assembly of claim 10, wherein the insulative element is configured to bond to an overmold during overmolding of the overmold adjacent the pre-molded cylindrical sub-assembly and over the plurality of elongated conductors.

17. The pre-molded cylindrical sub-assembly of claim 10, wherein the plurality of elongated conductors comprise one or more elongated conductors within insulation, and wherein the insulative element is configured to prevent contact between the interior surface of the cylindrical conductive element and insulation of the one or more elongated conductors.

18. The pre-molded cylindrical sub-assembly of claim 10, wherein the insulative element comprises a substantially cylindrical insulative element molded onto substantially all of the interior surface of the substantially cylindrical conductive element, wherein the substantially cylindrical insulative element defines a substantially continuous interior surface that defines the lumen of the pre-molded cylindrical sub-assembly.

19. The pre-molded cylindrical sub-assembly of claim 10, wherein the insulative element extends beyond at least one end of the cylindrical conductive element.

20. The pre-molded cylindrical sub-assembly of claim 19, wherein the insulative element tapers away from the end of the cylindrical conductive element.

21. The pre-molded cylindrical sub-assembly of claim 10, wherein the cylindrical conductive element defines a tangential hole through the interior surface and exterior surface of the cylindrical conductive element, the hole tangential to a longitudinal axis of the cylindrical conductive element, wherein the insulative element extends into the hole.

22. The pre-molded cylindrical sub-assembly of claim 10, wherein the exterior surface of the cylindrical conductive element and an interior surface of the insulative element define a longitudinal channel through the pre-molded cylindrical sub-assembly along a longitudinal axis of the pre-molded cylindrical sub-assembly.

23. The pre-molded cylindrical sub-assembly of claim 10, wherein the cylindrical conductive element is formed from a metal.

24. A method of manufacturing an implantable medical lead configured to conduct an electrical signal between an implantable medical device and tissue of a patient, the method comprising:
 manufacturing a plurality of pre-molded cylindrical sub-assemblies, wherein manufacturing each of the pre-molded cylindrical sub-assemblies comprises:
  forming a cylindrical conductive element with a conductive material to define a substantially continuous interior surface and a substantially continuous exterior surface; and insert-molding an insulative material onto the interior surface of the cylindrical conductive element to form an insulative element, wherein an interior of the insulative element defines a lumen of the pre-molded cylindrical sub-assembly;

longitudinally inserting more than one of a plurality of elongated conductors through at least one lumen of the plurality of pre-molded cylindrical sub-assemblies; and electrically connecting one of the elongated conductors to each of the cylindrical conductive elements of each of the pre-molded cylindrical sub-assemblies with the one or more elongated conductors within the lumen, wherein each of the cylindrical conductive elements is one of a connector configured to electrically connect the conductor to an implantable medical device, or an electrode configured to electrically connect the conductors to the tissue.

25. The method of claim 24, wherein insert-molding the insulative material onto the interior surface of the cylindrical conductive element comprises:

inserting the cylindrical conductive element into a mold;

inserting a mandrel into a lumen of the cylindrical conductive element; and delivering a flowable liner material comprising a hardenable organic polymer into the lumen of the cylindrical conductive element and over the mandrel, wherein the flowable liner material hardens to form the insulative element.

26. The method of claim 24, wherein the plurality of elongated conductors comprise one or more elongated conductors within insulation, and wherein the insulative element is configured to prevent contact between the interior surface of the cylindrical conductive element and the insulation of the one or more elongated conductors.

27. The method of claim 24, further comprising forming an overmold adjacent to the plurality of pre-molded cylindrical sub-assemblies and over the elongated conductors.

28. The method of claim 27, wherein forming the overmold comprises:

inserting the plurality of pre-molded cylindrical sub-assemblies with the elongated conductors within the respective lumens of the plurality of pre-molded cylindrical sub-assemblies into a mold that engages the exterior surfaces of the cylindrical conductive elements of the plurality of pre-molded cylindrical sub-assemblies; and delivering a flowable overmold material into the mold, wherein the overmold material hardens to form the overmold with an outer surface adjacent to the exterior surface of the cylindrical conductive elements of the plurality of pre-molded cylindrical sub-assemblies.

29. The method of claim 27, wherein the insulative elements are configured to center the one or more elongated conductors within the at least one or more lumens of the plurality of pre-molded cylindrical sub-assemblies during forming the overmold adjacent the plurality of pre-molded cylindrical sub-assemblies and over the elongated conductors.

30. The method of claim 27, wherein the insulative element is configured to bond to the overmold during forming the overmold adjacent the plurality of pre-molded cylindrical sub-assemblies and over the plurality of elongated conductors.

* * * * *